(12) United States Patent
Weber et al.

(10) Patent No.: US 11,268,134 B2
(45) Date of Patent: Mar. 8, 2022

(54) SENSOR APPARATUS AND METHOD FOR TESTING A SAMPLE

(71) Applicant: BOEHRINGER INGELHEIM VETMEDICA GMBH, Ingelheim am Rhein (DE)

(72) Inventors: Christoph Weber, Hannover (DE); Matthias Griessner, Hannover (DE); Nele Jenne, Hannover (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 25 days.

(21) Appl. No.: 16/142,071

(22) Filed: Sep. 26, 2018

(65) Prior Publication Data
US 2019/0100791 A1    Apr. 4, 2019

(30) Foreign Application Priority Data

Sep. 29, 2017  (EP) .................................... 17194120

(51) Int. Cl.
| | |
|---|---|
| *C12Q 1/6816* | (2018.01) |
| *G01N 33/53* | (2006.01) |
| *G01N 33/542* | (2006.01) |
| *G01N 33/543* | (2006.01) |
| *C12Q 1/68* | (2018.01) |

(52) U.S. Cl.
CPC ............. *C12Q 1/6816* (2013.01); *C12Q 1/68* (2013.01); *G01N 33/5302* (2013.01); *G01N 33/542* (2013.01); *G01N 33/54366* (2013.01)

(58) Field of Classification Search
CPC .......................... C12Q 1/6816; G01N 33/5302
See application file for complete search history.

(56) References Cited

U.S. PATENT DOCUMENTS

| | | | | |
|---|---|---|---|---|
| 4,581,333 A | * | 4/1986 | Kourilsky | C12Q 1/6813 435/6.18 |
| 5,096,669 A | | 3/1992 | Lauks et al. | |
| 7,914,655 B2 | | 3/2011 | Frey et al. | |
| 9,110,044 B2 | | 8/2015 | Gumbrecht et al. | |
| 2004/0081974 A1 | * | 4/2004 | Gao | C12Q 1/6837 435/6.11 |
| 2005/0164200 A1 | * | 7/2005 | Yabubayashi | C12Q 1/6837 435/5 |
| 2007/0059693 A1 | * | 3/2007 | Miller | C12Q 1/6818 435/6.11 |

(Continued)

FOREIGN PATENT DOCUMENTS

| | | |
|---|---|---|
| WO | 03035259 A2 | 5/2003 |
| WO | 2006125767 A1 | 11/2006 |

OTHER PUBLICATIONS

Wang et al, Graphenesheets, polyaniline and AuNPs based DNA sensor for lectrochemical determination of BCR/ABL fusion gene with functional hairpin probe, 2014, Biosensors and Bioelectronics, 51, 201-207. (Year: 2014).*

(Continued)

*Primary Examiner* — Narayan K Bhat
(74) *Attorney, Agent, or Firm* — David S. Safran; Roberts Calderon Safran & Cole, P.C.

(57) ABSTRACT

A sensor apparatus for testing a biological sample, a system making use thereof and a method for testing a biological sample with the sensor apparatus and system.

19 Claims, 10 Drawing Sheets

Specification includes a Sequence Listing.

(56) References Cited

U.S. PATENT DOCUMENTS

| | | | | |
|---|---|---|---|---|
| 2010/0209925 | A1* | 8/2010 | Ishibashi | C12Q 1/6837 435/6.16 |
| 2010/0248231 | A1* | 9/2010 | Wei | C12Q 1/6825 435/6.14 |
| 2014/0106441 | A1* | 4/2014 | Wang | C12Q 1/689 435/287.2 |
| 2014/0329713 | A1 | 11/2014 | Dai et al. | |
| 2018/0100188 | A1* | 4/2018 | Griessner | G01N 33/5438 |

OTHER PUBLICATIONS

Misra et al, Immobilization of self-quenched DNA hairpin probe with a heterobifunctional reagent on a glass surface for sensitive detection of oligonucleotides, 2009, Bioorganic & Medicinal Chemistry, 17, 5826-5833 (Year: 2009).*

Kjallman et al, Effect of Probe Density and Hybridization Temperature on the Response of an Electrochemical Hairpin—DNA Sensor, 2008, Anal. Chem., 80, 9460-9466 (Year: 2008).*

Klonoski et al, Enhanced detection of staphylococcal genomes in positive blood cultures using a polymeric enzyme complex, 2010, Analytical Biochemistry, 396, 284-289 (Year: 2010).*

Qiu et al, Cooperative Amplification-Based Electrochemical Sensor for the Zeptomole Detection of Nucleic Acids, 2013, Anal. Chem., 85, 8225-8231 (Year: 2013).*

D. Horejsh et al: "A molecular beacon, bead-based assay for the detection of nucleic acids by flow cytometry", Nucleic Acids Research, vol. 33, No. 2, 2005, e13.

Jing Zhang et al: "Electrogenerated Chemiluminescence DNA Biosensor based on Hairpin DNA Probe Labeled with Ruthenium Complex", Analytical Chemistry, vol. 80, No. 8, 1. Apr. 15, 2008, pp. 2888-2894.

Varun Rai et al: "Electrochemically amplified molecular beacon biosensor for ultrasensitive DNA sequence-specific detection of *Legionella* sp.", Biosensors and Bioelectronics, Elsevier BV, NL, Bd. 32, No. 1, Nov. 26, 2011 (Nov. 26, 2011), pp. 133-140. (DOI:10.1016/J.Bios.2011.11.046).

Qiang Su et al: "Molecular Beacon Modified Sensor Chips for Oligonucleotide Detection with Optical Readout", Langmuir, 30, 2014, p. 14360-14367.

* cited by examiner

SEQUENCE LISTING

<160> NUMBER OF SEQ ID NOS: 3

<210> SEQ ID NO 1
<211> LENGTH: 40
<212> TYPE: DNA
<213> ORGANISM: Artificial Sequence
<220> FEATURE:
<223> OTHER INFORMATION: synthetic

<400> SEQUENCE: 1
accagcctgc tagacaatgt tgccgttcga cttgcgcagg                    40

<210> SEQ ID NO 2
<211> LENGTH: 40
<212> TYPE: DNA
<213> ORGANISM: Artificial Sequence
<220> FEATURE:
<223> OTHER INFORMATION: synthetic

<400> SEQUENCE: 2
accagcctgc tagacaatgc tgccgttcga cttgcgcagg                    40

<210> SEQ ID NO 3
<211> LENGTH: 28
<212> TYPE: DNA
<213> ORGANISM: Artificial Sequence
<220> FEATURE:
<223> OTHER INFORMATION: synthetic

<400> SEQUENCE: 3
aacacaacaa tactgttyga rgtccacc                                 28

SENSOR APPARATUS AND METHOD FOR TESTING A SAMPLE

SEQUENCE LISTING

This specification includes a Sequence Listing uploaded on Apr. 20, 2020, as a 1 KB ASCII text file, filename 2020-04-20_second_amended_SEQLST_740126-000328_ST25.

BACKGROUND OF THE INVENTION

Field of the Invention

The present invention relates to the technical field of bioanalytics. The present invention relates in particular to a sensor apparatus for testing a biological sample.

Furthermore, the present invention relates to a method for detecting or identifying a target analyte.

Moreover, the present invention relates to an analysis system for testing a biological sample, and to the use of a sensor apparatus for detecting or identifying at least one analyte.

The present invention deals in particular with what are known as point-of-care systems, i.e., in particular, with mobile systems, devices and other apparatuses, and deals with methods for carrying out tests on a sample at the sampling site and/or independently or away from a central laboratory or the like. Preferably, point-of-care systems can be operated autonomously or independently of a mains network for supplying electrical power.

Description of Related Art

Increasingly, point-of-care systems are developed which are intended to make it possible, in particular in the field of veterinary medicine, for diseases and pathological conditions to be diagnosed rapidly and without complex laboratory tests, and which make it possible to optionally conclude whether further tests are required.

U.S. Pat. No. 5,096,669 discloses a point-of-care system for testing a biological sample, in particular a blood sample. The system comprises a single-use cartridge and an analysis device. Once the sample has been received, the cartridge is inserted into the analysis device in order to carry out the test. The cartridge comprises a microfluidic system and a sensor apparatus comprising electrodes, which apparatus is calibrated by means of a calibration liquid and is then used to test the sample.

Furthermore, International Patent Application Publication WO 2006/125767 A1 and corresponding U.S. Pat. No. 9,110,044 disclose a point-of-care system for integrated and automated DNA or protein analysis, comprising a single-use cartridge and an analysis device for fully automatically processing and evaluating molecular-diagnostic analyses using the single-use cartridge. The cartridge is designed to receive a sample, in particular blood, and in particular allows cell disruption, PCR and detection of PCR amplification products, which are bonded to capture molecules and provided with a label enzyme, in order for it to be possible to detect bonded PCR amplification products or nucleic-acid sequences as analytes in what is known as a redox cycling process.

The above-described point-of-care systems are all disadvantageous in that, in order to detect specific nucleic-acid sequences, primers provided with a label usually have to be used for the PCR so as to allow the nucleic-acid sequences to be detected.

The label is usually biotin, which bonds an enzyme, usually alkaline phosphatase, by means of streptavidin, such that the specific nucleic-acid sequence can be detected or identified as an analyte in a redox cycling process by converting a substrate.

However, the use of labelled primers, in particular biotinylated primers, is disadvantageous in that an additional PCR is required in order for the label to be attached to the nucleic-acid sequence. Furthermore, the labelled target acid nucleic sequences have to be selectively immobilized on capture molecules on sensor fields and/or sensor apparatuses provided specifically for this purpose in order that they can be separated from non-hybridized nucleic-acid sequences and/or unbonded labelled primers. If the hybridized nucleic-acid sequences are not completely separated from non-hybridized nucleic-acid sequences, erroneous signals are received because the enzymes are bonded to all labels. At best, this results only in the signal-to-noise ratio being worsened such that the detection reaction is less conclusive. However, it is also possible for incorrect signals to be generated and for pathogens, for example, to be supposedly detected that are not actually present in the tested sample.

This problem bears highly on point-of-care systems in particular, since rinsing and washing options are limited in the microfluidic systems usually used in point-of-care systems, and so bonded and unbonded nucleic acids and/or labelled primers can be separated to the required degree only with difficulty, in particular by comparison with laboratory tests.

In order to determine or identify nucleic-acid sequences, what are known as molecular beacons are also used in molecular biology. Molecular beacons are special hybridization probes or capture molecules for bonding specific nucleic-acid sequences, which usually include single-strand nucleic-acid sequences, and consist of three different functional regions, namely a stem, a loop and a fluorophore/quencher pair. Molecular beacons can assume a closed state and an open state. In the closed state, the nucleic-acid sequence forms a stem-loop or hairpin structure in which 5 to 10 base pairs are usually bonded to one another at each of the opposite ends of the nucleic-acid sequence and form the stem to which an unbonded nucleic-acid sequence, namely what is known as the loop, is attached. A fluorophore and a quencher are located at the ends of the nucleic-acid sequence.

In the closed state, the nucleic-acid sequence of the molecular beacon cannot be hybridized as a result of the stem-loop or hairpin structure. By heating and denaturing the molecular beacon, the hydrogen bonds of the stem are destroyed, such that the single-strand nucleic-acid sequence is unfolded and the nucleic-acid sequence is available for hybridization to target nucleic-acid sequences.

Furthermore, the molecular beacon, as mentioned above, usually comprises a fluorophore/quencher pair. The fluorophore/quencher pair is arranged such that, when the stem of the molecular beacon is closed, the fluorophore and quencher are in the immediate vicinity of one another and energy absorbed by the fluorophore is emitted to the quencher by means of fluorescence resonance energy transfer (FRET) and no fluorescence is observed. When the molecular beacon is open, the fluorophore and quencher are far apart, and therefore fluorescence occurs when the fluorophore is excited appropriately. By denaturing the molecular beacon and hybridizing said beacon to a target nucleic acid, the stem is prevented from closing again or a hairpin structure is prevented from being formed, and therefore a high-intensity fluorescence signal can be permanently observed. In this way, molecular beacons are suitable for detecting nucleic-acid sequences. In particular, since the fluorescence signal is observed only on hybridized molecular beacons, a very good signal-to-noise ratio is obtained and the detection sensitivity of tests using molecular beacons is correspondingly high.

Molecular beacons have therefore already also been used in sensor array chips for detecting nucleic-acid sequences.

For example, the scientific paper Q. Su, D. Wesner, H. Schönherr and G. Nöll, "Molecular Beacon Modified Sensor Chips for Oligonucleotide Detection with Optical Readout", Langmuir, 30, 2014, pages 14360-14367 describes molecular beacons which are bonded to the gold surface of sensor chips and the fluorescence signal of which is suppressed by quenching the fluorophore by means of the gold surface of the sensor chip when the molecular beacon is non-hybridized.

Furthermore, the scientific publication D. Horejsh, F. Martini, F. Poccia, G. Ippolito, A. Di Caro, M. R. Capobianchi, "A molecular beacon, bead-based assay for the detection of nucleic acids by flow cytometry", Nucleic Acids Research, vol. 33, no. 2, 2005, e13 relates to molecular beacons which are bonded to microspheres by means of biotin and streptavidin.

Although a very high level of detection sensitivity can be achieved using molecular beacons, detection by means of fluorescence is barely suitable for point-of-care systems, since spectroscopic evaluation can be carried out only with difficulty using mobile and in particular portable systems. Although it is possible to equip vehicles, for example, with spectroscopic evaluation systems of this kind, this system, however, contradicts the fundamental principle of the point-of-care system in which preferably all components of the analysis system can be carried in a mobile manner.

Thus, the prior art still lacks a sensor system and/or an analysis system which has higher sensitivity and a lower error rate by comparison with existing systems, and which can furthermore be used in mobile systems is not contained in the prior art either.

SUMMARY OF THE INVENTION

One object of the present invention is therefore to provide an apparatus, in particular a sensor apparatus, which is suitable for use in point-of-care systems and which has a significantly improved signal-to-noise ratio by comparison with systems from the prior art.

A further object of the present invention is to provide a definite and reproducible method for detecting target analytes, in particular nucleic-acid sequences.

Yet another object of the present invention is to provide a method which makes it possible to determine nucleic-acid sequences in point-of-care systems.

According to a first aspect of the present invention, a subject of the present invention is therefore a sensor apparatus as described herein.

According to a second aspect of the present invention, a further subject of the present invention is a method for detecting or identifying an analyte as described herein.

Finally, according to another aspect of the present invention, a further subject of the present invention is an analysis system as described herein.

It goes without saying that particular embodiments or the like referred to in the following, which are described only in connection with one aspect of the invention, also apply correspondingly in relation to the other aspects of the invention, without the need for this to be expressly mentioned.

It should further be noted that all relative quantities or percentages referred to hereinafter, in particular quantities stated in terms of weight, are intended to be selected by a person skilled in the art in the context of the present invention such that the sum of the ingredients, additives or auxiliaries or the like is always 100%, or 100 wt. %. However, this is obvious to a person skilled in the art.

Moreover, a person skilled in the art can deviate from the numbers, ranges or quantities stated hereinafter on a case-by-case basis, and depending on application, without departing from the scope of the present invention.

Furthermore, all of the stated parameters, or the like, referred to in the following can be determined or established by standardized or explicitly indicated determination methods, or determination methods familiar to a person skilled in the art per se.

That being said, the subject matter of the present invention is explained in more detail below.

According to a first aspect of the present invention, a subject of the present invention is thus a sensor apparatus for testing a biological sample, the sensor apparatus comprising at least one capture molecule, in particular a hairpin probe, for bonding an analyte, in particular a target nucleic-acid sequence, the capture molecule being bonded to a surface of the sensor apparatus and comprising a label for detecting the analyte.

Within the meaning of the present invention, capture molecules are in particular nucleic-acid sequences, in particular DNA sequences and/or RNA sequences, i.e., so-called capture nucleic-acid sequences. The capture molecules are preferably in the form of hairpin probes. In particular, capture molecules are designed to bond and/or immobilize corresponding analytes of the sample.

Within the meaning of the present invention, capture nucleic-acid sequences are in particular capture molecules based on long (single-stranded) nucleic-acid sequences, in particular DNA sequences and/or RNA sequences, particularly preferably having more than 20 or 30 bases and/or fewer than 5000 or 1000 bases. In particular, capture nucleic-acid sequences are designed to bond corresponding target nucleic-acid sequences, in particular target DNA sequences and/or target RNA sequences, which are particularly preferably at least substantially of the same length.

In the context of the present invention, a hairpin probe (hairpin sensor) or stem-loop probe (stem-loop sensor) is understood to mean a hybridization probe which comprises a single-strand nucleic-acid sequence and is non-hybridized in a hairpin structure (or stem-loop structure) at room temperature.

In this case, the nucleic-acid sequence of the hairpin probe is subdivided into or comprises two stem parts and an intermediate loop which usually comprises a nucleic-acid sequence for bonding an analyte, in particular a target nucleic-acid sequence; however, it is also possible that also the nucleic-acid sequences which form the stem bond the analyte; all that matters is that the nucleic-acid sequence of the probe forms a hairpin or stem-loop structure. The nucleic-acid sequences of the stem, which are located in front of and behind the nucleic-acid sequence of the loop, bond to one another via hydrogen bridges or hydrogen bonds such that the stem is closed and the nucleic-acid sequence of the loop is not available for bonding to a target analyte. The nucleic-acid sequences of the stem usually each comprise four to ten nucleic acids which are each arranged ahead of and after the nucleic-acid sequence of the loop which preferably comprises 30 to 100 nucleic acids. If the nucleic-acid sequence for bonding and/or hybridizing to the target analyte is already present in the hairpin structure, it is possible to dispense with special nucleic-acid sequences for the stem. The hydrogen bonds of the stem can be broken by energy being supplied, in particular by means of an increase in temperature, such that the nucleic-acid sequence of the loop can be hybridized to suitable nucleic-acid sequences.

In the context of the present invention, the capture molecule, in particular the hairpin probe, is bonded to the surface of the sensor apparatus. In this connection, it is preferable for the hairpin probe to be bonded to the surface of the sensor apparatus by means of the stem and optionally further chemical groups acting as spacers.

In the context of the present invention, a label is understood to mean a molecule, molecule fragment or atom which forms part of the capture molecule or is bonded thereto, and which can be specifically detected or identified chemically and/or physically.

In the context of the present invention, the label is preferably bonded to the part of the stem, in particular the nucleic-acid sequence of the stem or the nucleic-acid sequence of the loop, which is spaced apart from the bonding site of the capture molecule, in particular the hairpin probes, to the surface of the sensor apparatus.

In the context of the present invention, the sensor apparatus is preferably a sensor array, in particular an array chip, for testing biological samples, in particular for detecting or identifying nucleic-acid sequences, i.e., a nucleic-acid array.

In the context of the present invention, particularly good results are achieved if the sensor apparatus comprises a plurality of capture molecules, in particular capture nucleic-acid sequences, preferably hairpin probes, such that, in the context of a test on a sample, at least two, in particular a plurality of nucleic-acid sequences can be tested for and/or said sequences can be detected or identified.

Putting a label on a capture molecule, in particular on a hairpin probe, makes it possible for a real-time PCR to be carried out without having to use labelled primers, which significantly simplifies the method and makes it less complex and thus more cost-effective to carry out said method. Furthermore, owing to the absence of labelled primers, in particular biotinylated primers, the signal-to-noise ratio during the detection reaction is significantly improved, since unreacted labelled primers and/or non-hybridized labelled nucleic-acid sequences do not have to be completely removed from the sensor apparatus before the detection of bonded and/or hybridized nucleic-acid sequences takes place.

Moreover, a further PCR for labelling the target nucleic-acid sequence can also be dispensed with. The sensor apparatus according to the invention and the detection method made possible by said sensor apparatus therefore allows nucleic-acid sequences to be determined or identified in a significantly more precise and clearer manner such that, in the context of the present invention, significantly lower amounts of analyte substance in the biological sample can be operated with.

The sensor apparatus according to the invention can further be used in point-of-care systems without restrictions.

The capture molecule is usually bonded to the surface of the sensor apparatus by means of a bonding unit. In the context of the present invention, it is preferable for the capture molecule to be chemically bonded to the surface of the sensor apparatus by means of the bonding unit. In the context of the present invention, the bonding unit is preferably understood to mean a chemical functionality, a chemical group or a combination of different chemical groups, by means of which the actual capture molecule, in particular the capture nucleic-acid sequence, preferably hairpin probe, is bonded to the surface of the sensor apparatus. In the simplest case, the bonding unit is a simple chemical functionality, such as a sulfide bridge or an ether functionality; however, it is also possible for the bonding unit to consist of a chemical functionality, such as a sulfide functionality or ether functionality, which chemically bonds to the surface of the sensor apparatus, and to which an aliphatic and/or aromatic hydrocarbon functional group or another inorganic or organic functional group is attached, which functional group is connected to the actual capture molecule.

The bonding unit usually comprises functional chemical groups for bonding the capture molecule to the surface of the sensor apparatus. Particularly good results are achieved in this regard if the functional chemical groups for bonding the capture molecules are selected from the group of amides, esters, urethanes, ethers, sulfides, sulfoxides and sulfones. In this context, it has proven particularly expedient for the chemical groups to be sulfides, i.e., sulfide bridges, which connect the preferably organic capture molecule to the usually inorganic surface of the sensor apparatus. The surface of the sensor apparatus is usually formed of a thin metal layer, such as a gold layer. In particular, if the surface of the sensor apparatus is made of other inorganic materials, such as silicon dioxide, the bonding unit may be connected to the surface of the sensor apparatus by means of ether functionalities.

Further, the bonding unit may usually comprise at least one spacer. The spacer is usually an aromatic and/or aliphatic organic group, in particular a hydrocarbon functional group, which connects the chemical functionality for bonding the capture molecule to the surface of the sensor apparatus, such as an ether group or a sulfide group, to the actual capture molecule.

The length of the spacer is selected in particular such that the analyte, in particular the target nucleic acid, can easily bond to the capture molecule; however, the spacer is preferably short enough that the label, for example, is bonded close enough to the surface of the sensor apparatus that it is sterically shielded from reactions with substrates or enzyme conjugates and is only far enough from the surface of the sensor apparatus for a signal to be generated when the analyte is bonded, i.e., hybridized. If the bonding unit comprises a spacer, it has proven expedient for the spacer to comprise 1 to 50, in particular 1 to 20, preferably 2 to 15, more preferably 3 to 10, carbon atoms.

In regard to the label, particularly good results are achieved in the context of the present invention if the label, in particular a marker molecule, can be detected or identified directly by means of physical and/or chemical methods, in particular electrical or electrochemical measuring methods, or indirectly, after reacting with further molecules, by means of chemical and/or physical methods, in particular electrical and/or electrochemical methods. Examples of molecules or marker molecules that can be detected by means of direct electrical measurements are, for example, methylene blue and ferrocene, which are bonded to the capture molecule. When using ferrocene or methylene blue as the label or marker molecule, the capture molecule is designed such that, when the capture molecule is non-hybridized, the label is deposited near to a surface of the sensor apparatus, which preferably consists of a metal, in particular a gold layer, such that there is a specific potential between the label and the surface that can be measured. By hybridizing the capture molecule, the label is moved away from the surface of the sensor apparatus, as a result of which the potential changes, which can be measured directly as a change in electrical voltage.

Furthermore, it is however also possible for the label or marker molecule to be a molecule which can react with enzyme conjugates which in turn convert substrates, and this can be detected by means of electrochemical measurements. Examples of this type of labels or marker molecules are biotin or dioxigenin, which, when the capture molecule or hairpin probe is hybridized, bond to enzymes or enzyme conjugates, such as streptavidin-alkaline phosphatase or horseradish peroxidase, and convert substrates, for example hydrogen peroxide or tetramethylbenzidine, in redox reactions, and this can be detected by means of electrical potential measurements.

The label is usually selected from marker molecules, in particular marker molecules that can bond enzyme conjugates or the components thereof.

According to a particularly preferred embodiment of the present invention, the label is biotin. Biotin can bond a streptavidin enzyme conjugate, for example, which converts detectable substrates. In particular, substrates of this kind or the conversion products thereof can be detected or identified by means of simple electrical measurement, preferably redox cycling methods.

If enzyme conjugates or the components thereof, in particular biotin, are used as the label, the sensor apparatus according to the invention is extremely suitable for use in mobile point-of-care systems, since the entire analysis and evaluation unit can be integrated directly in the point-of-care system.

In the context of the present invention, the label is preferably not a fluorescence dye (fluorophore).

In the context of the present invention, particularly good results are achieved if the capture molecule comprises a nucleic-acid sequence. In this regard, particularly good results are achieved if the nucleic-acid sequence comprises 20 to 100, preferably 25 to 70, particularly preferably 30 to 50, nucleic acids for bonding an analyte, in particular a target nucleic acid. In the case of a hairpin probe, the aforementioned nucleic-acid sequence corresponds in particular to the aforementioned loop, to each end of which the nucleic acids of the stem are attached.

In the context of the present invention, it is preferable for the label to be able to assume at least two, in particular two, states which can be distinguished, in particular clearly distinguished, by means of chemical and/or physical methods, in particular measuring methods. In this regard, it is preferable for the label to be able to assume the distinguishable states in particular depending on a change in the state of the capture molecule.

In the context of the present invention, it is therefore preferable for the label to assume a state which is clearly different from the unbonded state of the capture molecule, in particular by bonding the target nucleic acid to the capture molecule, i.e., by hybridization.

In this regard, it is particularly preferable for the two states to be clearly detectable by means of chemical or physical methods such that the detection reaction is specific and unique to specific analytes, in particular target nucleic-acid sequences. In this regard, it is not necessarily required that it is possible for the change in state to be directly observed or measured; instead, the process may also be such that, for example, when an analyte is bonded to the capture molecule, the label is available for bonding to a further molecule, in particular an enzyme conjugate, which in turn converts substrates, and the conversion products of the substrate can be determined.

The change in the state of the label can be induced by a change in the conformation of the capture molecule caused by the bonding of the analyte, as a result of which a changed electrical situation of the label, for example a steric hindrance of the bonding of the label to further molecules, is created, for example in the case of electrical probes, such as ferrocene or methylene blue, of which the electric potential changes together with the distance from the surface of the electrode.

In the context of the present invention, particularly good results are achieved if the label assumes the distinguishable states depending on the bonding of a target analyte. Therefore, it is preferable for it to be possible to clearly distinguish the unbonded state of the capture molecule from a bonded state of the capture molecule, such that specific detection reactions for the target analytes, in particular target nucleic-acid sequences, can be carried out.

The capability and/or readiness of the capture molecule to bond the analyte, in particular the target nucleic acid, can preferably be set or adjusted, in particular increased, by controlling or feedback controlling the temperature. In this regard, particularly good results are achieved if the temperature is set or adjusted in the range of from 10 to 100° C., in particular from 20 to 100° C., preferably from 30 to 99° C., more preferably from 40 to 98° C. Capture molecules, in particular hairpin probes, are also in particular denatured in this temperature range, such that said molecules are available, to a greater extent, for the subsequent reaction with analytes.

According to a preferred embodiment of the present invention, the different states of the label can be detected or identified by means of chemical and/or physical methods selected from the group of electrical measurements and electrochemical methods. As already mentioned previously, in the context of the present invention, it may be that the change in the state of the label is not measured directly, but is instead measured indirectly, for example, by the label being chemically bonded to enzyme conjugates and said conjugates converting substrates, which conversion can in turn be detected.

According to a particularly preferred embodiment of the present invention, the capture molecule, in particular the hairpin probe, is bonded to the surface of a sensor field of the sensor apparatus. In this regard, it is particularly preferable for the capture molecule, in particular the hairpin probe, to be bonded to the surface of a sensor field of a sensor array of the sensor apparatus.

In the context of the present invention, it is particularly preferable for different capture molecules, preferably hairpin probes, to be bonded to different sensor fields. As a result, it is possible for a plurality of microbiological detection reactions to be carried out during testing, i.e., during testing of a sample.

According to a second aspect of the present invention, a further subject of the present invention is a method for detecting or identifying an analyte, in particular a target nucleic-acid sequence, by bonding the analyte to capture molecules of a sensor apparatus, the capture molecules being bonded to the sensor apparatus and comprising at least one label for detecting the analyte, the analyte bonding to the capture molecules, as a result of which the state of the label changes and the change in the state of the label is detected or identified by means of chemical and/or physical methods.

In this regard, the analyte usually bonds to the capture molecules in a first method step. The change in the state of the label is usually detected by means of chemical and/or physical methods in a method step which follows the first method step. As already mentioned in connection with the sensor apparatus according to the invention, the detection can take place directly or indirectly, i.e., by direct physical measurement or for example by chemical conversion of the label and subsequent measurements.

Advantageously, when carrying out the method according to the invention, in order to bond the analytes to the capture molecules, in particular in a first method step, the sensor apparatus, in particular the sensor field, is preferably treated, in particular wetted, with a solution or dispersion which contains the analyte. Advantageously, in this regard, the concentration of the analyte, in particular of the target nucleic acid or the target nucleic-acid sequences, is preferably significantly increased by PCR such that both qualitative and quantitative detection is possible.

In regard to carrying out the method according to the invention, it has also proven expedient for the temperature to be set at or adjusted to values in the range of from 20 to 100° C., in particular from 30 to 100° C., preferably from 40 to 99° C., more preferably from 45 to 98° C., particularly preferably from 50 to 96° C., for bonding the analytes to the capture molecules, in particular in the first method step. At the above-mentioned temperatures, on the one hand, capture molecules in the form of hairpin probes are denatured, i.e., opened, and are available for bonding, in particular hybridization, to the analytes, in particular the target nucleic acids. Furthermore, the preferred temperatures for hybridizing the analytes, in particular the target nucleic acids, are also within the mentioned temperature intervals.

According to a particularly preferred embodiment of the present invention, the temperature is set or adjusted in the form of a dynamic temperature regime, in particular a decreasing temperature regime, in order to bond the analytes to the capture molecules, in particular in the first method step. In this case, a decreasing temperature regime is understood to mean that the temperature is increased significantly at the beginning and then decreases further during the method or process. As a result of a significant increase in temperature, all of the capture molecules, in particular the hairpin probes, are denatured and thus opened. During a subsequent cooling, the specific hybridization temperatures are subsequently run through or reached such that the target-nucleic acids selectively bond to the specific capture molecules, in particular hairpin probes. If the temperature drops further, all of the non-hybridized hairpin probes then close again such that the labels thereof are not available for detection.

Particularly good results are achieved if the starting temperature of the temperature regime is set at or adjusted to values in the range of from 50 to 100° C., in particular from 55 to 99° C., preferably from 60 to 99° C., more preferably from 70 to 95° C. At the same time, it has proven expedient for the end temperature of the temperature regime to be set at or adjusted to values in the range of from 20 to 80° C., in particular from 30 to 70° C., preferably from 40 to 65° C., more preferably from 50 to 60° C. Furthermore, it may likewise be provided for cooling to ambient temperature or room temperature. However, without active cooling, this is associated with a significant loss of time, and therefore usually there is cooling only to temperatures in the aforementioned range.

After the analyte has been bonded to the capture molecules, in particular after the first method step, the sensor apparatus, in particular the sensor field, is preferably treated, in particular wetted, with a detector, in particular a detector molecule, and/or a substrate. By bonding a detector, in particular a detector molecule, which preferably reacts chemically with the label L, it is in particular possible to convert substrates, it being possible to subsequently detect the conversion or conversion products.

A preferred embodiment according to the present invention is a method for detecting or identifying an analyte, in particular a target nucleic-acid sequence, by bonding an analyte to capture molecules of a sensor apparatus, the capture molecules, in particular hairpin probes, being bonded to the sensor apparatus and comprising at least one label for detecting the analyte, in which (a) in a first method step, the sensor apparatus is treated, in particular wetted, with a solution or dispersion which contains the analyte, the analyte being bonded to the capture molecules, in particular the hairpin probes, (b) in a second method step, which follows the first method step (a), a detector, in particular a detector molecule, is bonded to the label, and (c) in a third method step, which follows the second method step (b), the detector is detected by means of chemical and/or physical methods.

All of the features of the advantageous embodiment, which has been mentioned previously in the general description of the method according to the invention and the sensor apparatus according to the invention, can also be applied to this particular embodiment.

For more extensive details regarding the method according to the invention, reference can be made to the explanations above with respect to the sensor apparatus according to the invention, which explanations apply correspondingly in relation to the method according to the invention.

According to a third aspect of the present invention, yet another subject of the present invention is the use of a sensor apparatus as described above for detecting or identifying at least one analyte, in particular a target nucleic acid sequence, in a biological sample.

For more extensive details regarding this aspect of the invention, reference can be made to the explanations above with respect to the other aspects of the invention, which explanations apply correspondingly in relation to the use according to the invention.

According to a fourth aspect of the present invention, yet another subject of the present invention is an analysis system for testing a biological sample containing at least one analyte, in particular a target nucleic-acid sequence, and which comprises a sensor apparatus as described above.

For more extensive details regarding the analysis system according to the invention, which relate to the sensor apparatus, reference can be made to the explanations above with respect to the other aspects of the invention so as to avoid unnecessary repetition, which explanations apply correspondingly to the analysis system according to the invention.

The proposed analysis system for testing a biological sample comprises a sensor apparatus and in particular a cartridge comprising a sensor apparatus for identifying or detecting analytes, in particular target analytes, of the sample, the cartridge and/or sensor apparatus preferably being provided with capture molecules for capturing and/or bonding the analytes.

The sensor apparatus preferably comprises a plurality of sensor fields and/or electrode pairs which each permit an independent measurement and/or detection.

The individual sensor fields and/or electrode pairs or individual electrodes are preferably each provided with capture molecules such that assays or detections can be carried out in order to homogeneously or simultaneously detect or identify a plurality of analytes, in particular target nucleic-acid sequences.

Particularly preferably, the analysis system and/or an analysis device of the analysis system comprises a temperature-control apparatus for temperature-controlling the sensor apparatus or a sensor arrangement formed thereby and/or the cartridge and/or a fluid contained therein, preferably in order to denature the analytes and/or the capture molecules, in particular the hairpin probes, by means of a corresponding effect of heat, and to thereby provide for bonding between analytes and capture molecules.

The term "denaturing" is preferably understood to mean a structural change to molecules, in particular nucleic-acid sequences. During denaturing, the spatial structure and/or 3D structure of the molecules is preferably destroyed. In particular, denaturing results in intramolecular bonds in the capture molecules, in particular hairpin probes and target nucleic-acid sequences, being broken and the molecules being available for hybridization.

Denaturing is preferably brought about by the effect of heat. Denaturing can, however, also be brought about by other physical influences and/or by chemical influences.

Denaturing can in particular result from a direct effect of heat, for example from directly heating the sensor apparatus, and/or from an indirect effect of heat, for example from conducting a heated fluid.

The analysis device and/or the cartridge and/or the sensor apparatus is preferably designed for carrying out a nucleic-acid assay. In particular, the sensor apparatus comprises capture nucleic-acid sequences, in particular hairpin probes, as capture molecules, in particular in order to bond analytes, in particular target nucleic-acid sequences, which correspond to the capture nucleic-acid sequences.

The sensor arrangement or sensor apparatus is preferably designed for electrochemically detecting analytes bonded to the capture molecules.

The sensor apparatus preferably comprises (exactly) one sensor array having a plurality of sensor fields and/or electrodes (or electrode pairs), the sensor fields and/or electrodes (or electrode pairs) in particular each being provided with capture molecules.

The capture nucleic-acid sequences are preferably immobilized on the sensor apparatus, in particular on the sensor array and/or the sensor fields. The capture nucleic-acid sequences can bond and/or immobilize analytes based on target nucleic-acid sequences, preferably by hybridization. The immobilized analytes can be identified or detected by means of subsequent electrochemical measurement and/or redox cycling, and/or fluorescence measurement.

It is proposed that the analysis system and/or the cartridge and/or the sensor apparatus makes particularly comprehensive testing of the sample possible, in particular the detection of target nucleic-acid sequences. Thus, a particularly large number of and/or particularly different and/or comprehensive tests can advantageously be carried out on the sample and/or a plurality of diseases and/or pathogens can be detected or identified in the sample.

The analysis system is preferably portable, mobile and/or is a point-of-care system and/or can be used in particular at the sampling site and/or away from a central laboratory and/or can be operated autonomously and/or independently of the mains, in particular independently of a mains power supply, for example by accumulators, batteries and/or other power storage means.

The analysis system preferably comprises an analysis device and a cartridge for testing the sample, the cartridge preferably being designed for receiving the sample and the analysis device preferably being designed for receiving the cartridge.

The term "analysis device" is preferably understood to mean an instrument which is in particular mobile and/or can be used on site, and/or which is designed to chemically, biologically and/or physically test and/or analyze a sample or a component thereof, preferably in and/or by means of a cartridge. In particular, the analysis device controls the pretreatment and/or testing of the sample in the cartridge.

Particularly preferably, the analysis device is designed to receive the cartridge or to connect said cartridge electrically, thermally, mechanically and/or pneumatically.

The term "cartridge" is preferably understood to mean a structural apparatus or unit designed to receive, to store, to physically, chemically and/or biologically treat and/or prepare and/or to measure a sample, preferably in order to make it possible to detect, identify or determine at least one analyte, in particular a nucleic-acid sequence, of the sample.

A cartridge within the meaning of the present invention preferably comprises a fluid system having a plurality of channels, cavities and/or valves for controlling the flow through the channels and/or cavities.

In particular, within the meaning of the present invention, a cartridge is designed to be at least substantially planar and/or card-like, in particular is designed as a (micro)fluidic card and/or is designed as a main body or container that can preferably be closed and/or said cartridge can be inserted and/or plugged into a proposed analysis device when it contains the sample.

The term "assay" is preferably understood to mean an in particular molecular-biological test for detecting or identifying at least one analyte in a sample. In particular, at least one analyte in a sample can be qualitatively and/or quantitatively detected or identified by means of an assay or by carrying out an assay. A plurality of method steps are preferably required to (fully) carry out an assay. Preferably, within the meaning of the present invention, when carrying out an assay, a sample is pretreated with one or more reagents and the pretreated sample is tested, in particular at least one analyte in the sample being detected or identified.

Within the meaning of the present invention, an assay is in particular a nucleic-acid assay for detecting or identifying a target nucleic-acid sequence, in particular a target DNA sequence and/or target RNA sequence, particularly preferably by bonding to corresponding capture nucleic-acid sequences, in particular hairpin probes.

According to a further embodiment of the present invention, the sensor apparatus comprises a plurality of types of capture molecules, the capture molecules being selected from a selection group consisting of capture proteins, capture aptamers and/or capture nucleic-acid sequences, in particular in order to bond analytes which correspond to the capture proteins, in particular target proteins and/or target hormones, to bond analytes which correspond to the capture nucleic-acid sequences, in particular target nucleic-acid sequences, and/or to bond analytes which correspond to the capture aptamers, in particular target proteins, low-molecular substances, steroids, organophosphates or other target analytes.

According to a specific embodiment, the sensor apparatus comprises both capture proteins and capture nucleic-acid sequences as capture molecules, in particular in order to bond analytes which correspond to the capture proteins, in particular target proteins and/or target hormones, and to bond analytes which correspond to the capture nucleic-acid sequences, in particular target nucleic-acid sequences.

According to another embodiment, the sensor apparatus comprises both capture aptamers and capture nucleic-acid sequences as capture molecules, in particular in order to bond analytes which correspond to the capture aptamers, in particular target proteins, low-molecular substances, steroids, organophosphates or other analytes, and to bond analytes which correspond to the capture nucleic-acid sequences, in particular target nucleic-acid sequences.

According to another particular embodiment, the sensor apparatus comprises capture proteins, capture aptamers and capture nucleic-acid sequences.

According to another aspect of the present invention, which can also be implemented independently, the analysis system and/or the cartridge and/or sensor apparatus is designed to carry out a plurality of (different) assays, in particular sequentially, the assays preferably being selected from a selection group consisting of a protein assay for detecting or identifying an analyte, in particular a target protein, particularly preferably by means of a capture protein, a nucleic-acid assay for detecting or identifying an analyte, in particular a target nucleic-acid sequence, particularly preferably by means of a capture nucleic-acid sequence, and/or an aptamer assay for detecting or identifying an analyte, in particular a target protein or another analyte that is preferably different from the target protein, particularly preferably by means of a capture aptamer.

Particularly preferably, a plurality of assays are carried out, selected from at least two assays from the selection group consisting of a protein assay for detecting or identifying a target analyte, in particular a target protein or target hormone, particularly preferably by means of a capture protein, and/or a nucleic-acid assay for detecting or identifying an analyte, in particular a target nucleic-acid sequence, particularly preferably by means of a capture nucleic-acid sequence, and/or an aptamer assay for detecting or identifying an analyte, in particular a target protein and/or another analyte that is preferably different from the target protein, particularly preferably by means of a capture aptamer, the protein assay preferably being carried out before the nucleic-acid assay, and/or the nucleic-acid assay preferably being carried out before the aptamer assay. This makes comprehensive, rapid and/or precise testing of the sample possible.

In particular, a protein assay and/or an aptamer assay for detecting or identifying an analyte or target protein as the analyte and a nucleic-acid assay for detecting or identifying a target nucleic-acid sequence as the analyte are carried out sequentially or successively in a (single) cartridge and/or sensor apparatus. However, other analytes, such as low-molecular substances, steroids, organophosphates or the like, can also be detected or identified, in particular by means of the aptamer assay.

According to this embodiment of the present invention, the sample is preferably split into portions, in particular in a cartridge, a plurality of (different) assays selected from at least two assays from the selection group consisting of a protein assay, an aptamer assay and/or a nucleic-acid assay being carried out in the same cartridge and/or sensor apparatus. This makes comprehensive, rapid and/or precise testing of the sample possible.

The above-mentioned embodiments, aspects and features of the present invention and the embodiments, aspects and features of the present invention that will become apparent from the claims and the following description can in principle be implemented independently from one another, but also in any combination or order.

Other aspects, advantages, features and properties of the present invention will become apparent from the claims and the following description of a preferred embodiment with reference to the drawings, in which:

DETAILED DESCRIPTION OF THE INVENTION

In the figures, which are only schematic and sometimes not to scale, the same reference signs are used for the same or similar parts and components, corresponding or comparable properties and advantages being achieved even if these are not repeatedly described.

Figure 1:
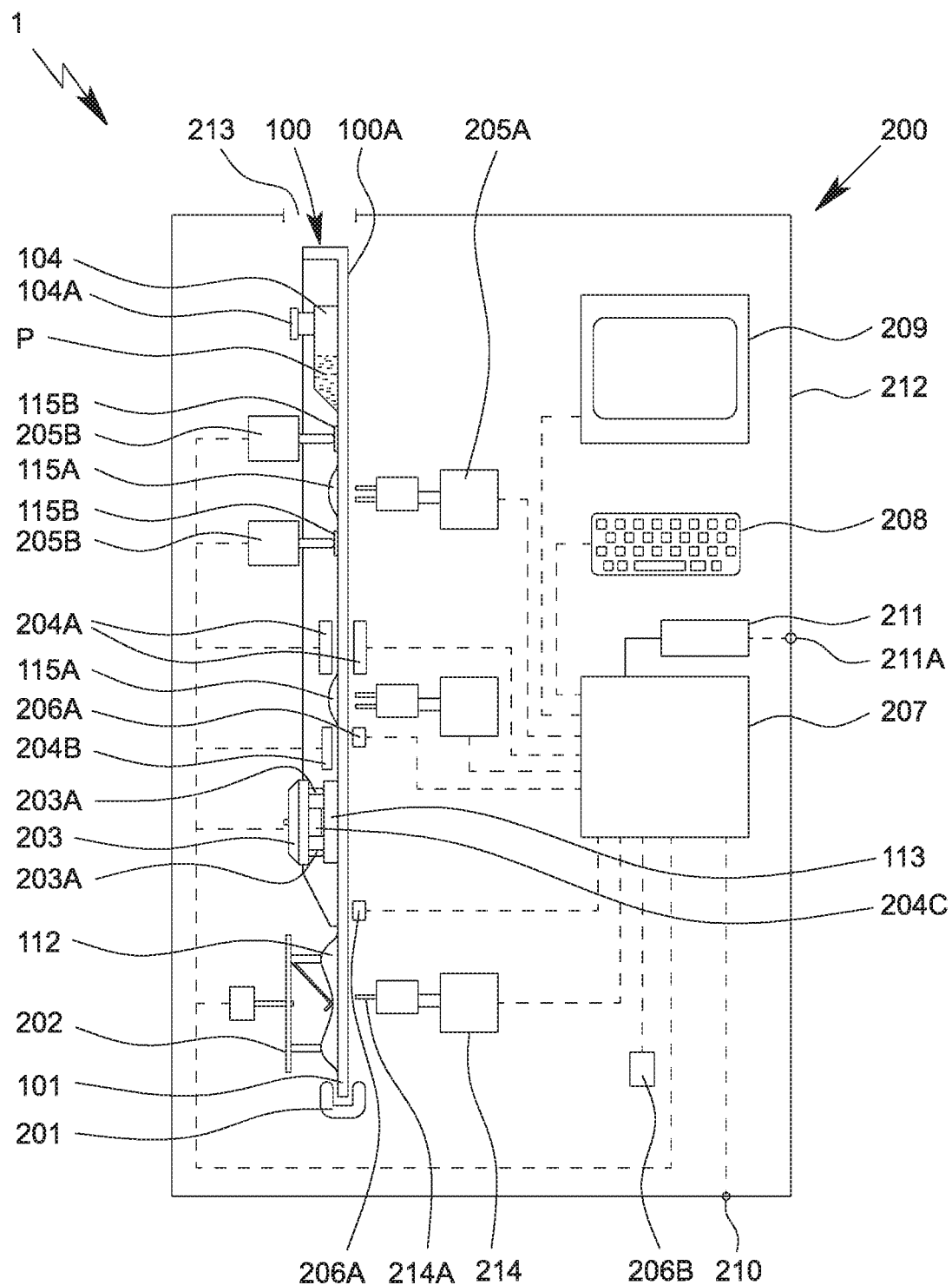
FIG. 1 is a schematic view of a proposed analysis system comprising a proposed analysis device and a proposed cartridge received in the analysis device.

FIG. 1 is a highly schematic view of a proposed analysis system 1 and analysis device 200 for testing, in particular, a biological sample P, preferably by means of or in an apparatus or cartridge 100.

Figure 2:
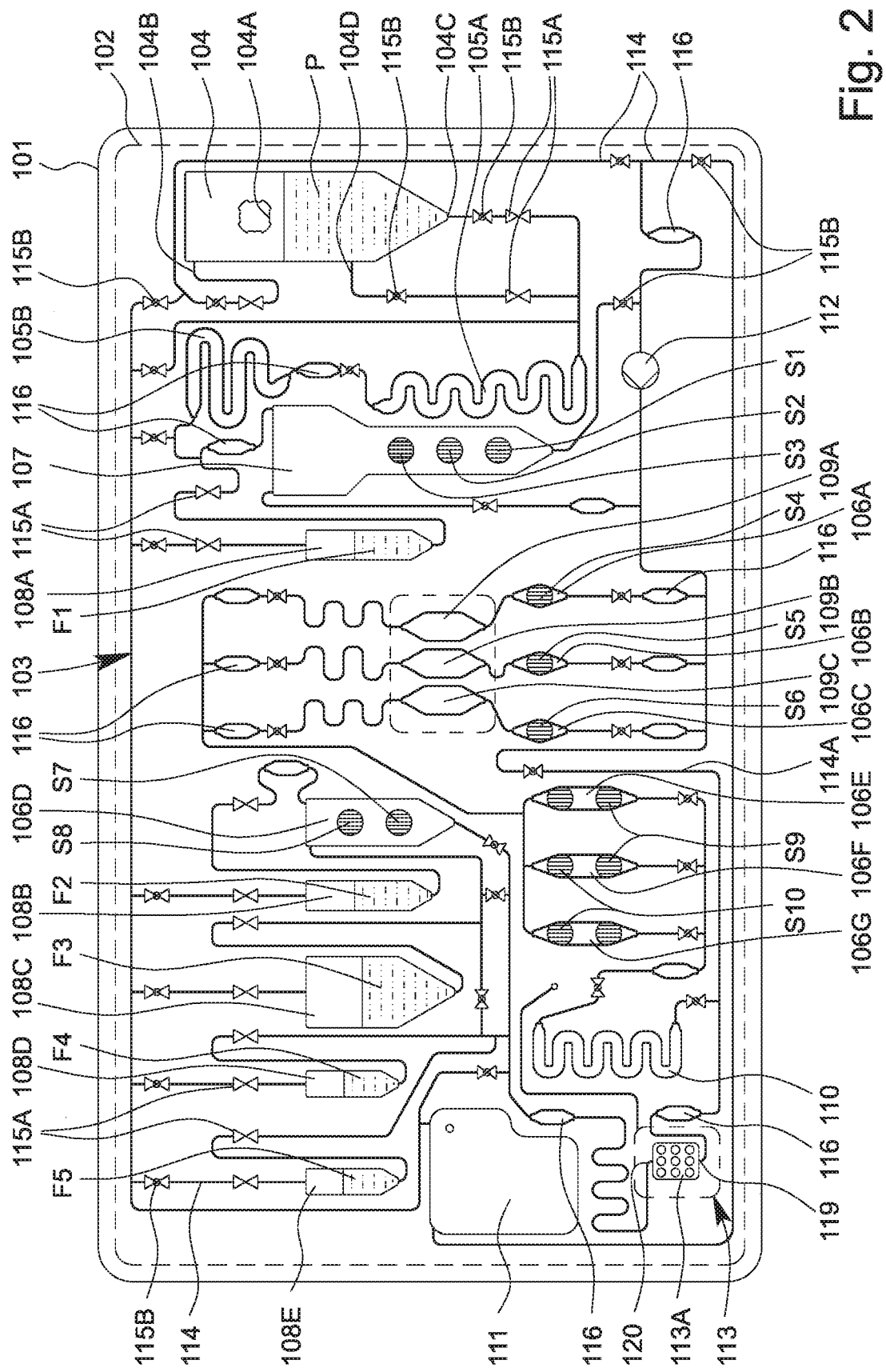
FIG. 2 is a schematic view of the cartridge.

FIG. 2 is a schematic view of a preferred embodiment of the proposed apparatus or cartridge 100 for testing the sample P. The apparatus or cartridge 100 in particular forms a handheld unit, and in the following is merely referred to as a cartridge 100.

The term "sample" is preferably understood to mean the sample material to be tested, which is in particular taken from a human or animal. In particular, within the meaning of the present invention, a sample is a fluid, such as saliva, blood, urine or another liquid, preferably from a human or animal, or a component thereof. Within the meaning of the present invention, a sample may be pretreated or prepared if necessary, or may come directly from a human or animal or the like, for example. A food sample, environmental sample or another sample may optionally also be tested, in particular for environmental analytics, food safety and/or for detecting other substances, preferably natural substances, but also biological or chemical warfare agents, poisons or the like.

A sample within the meaning of the present invention preferably contains one or more analytes, it preferably being possible for the analytes to be identified or detected, in particular qualitatively and/or quantitatively determined. Particularly preferably, within the meaning of the present invention, a sample has target nucleic-acid sequences as the analytes, in particular target DNA sequences and/or target RNA sequences. Particularly preferably, at least one disease, pathogen and/or other substances can be detected or identified in the sample P by qualitatively and/or quantitatively determining the analytes.

Preferably, the analysis system 1 or analysis device 200 controls the testing of the sample P in particular in or on the cartridge 100 and/or is used to evaluate the testing or the collection, processing and/or storage of measured values from the test.

By means of the proposed analysis system 1 and/or analysis device 200 and/or by means of the cartridge 100 and/or using the proposed method for testing the sample P, preferably an analyte, in particular a target nucleic-acid sequence ZN (see FIGS. 8 to 11), of the sample P, in particular a (certain) nucleic-acid sequence or target nucleic-acid sequence can be determined, identified or detected. Particularly preferably, a plurality of analytes of the sample P, in particular a plurality of different target nucleic-acid sequences ZN can be determined, identified or detected, in particular on a cartridge 100. The analytes are, in particular, detected, identified and/or measured not only qualitatively, but, alternatively or additionally, particularly preferably also quantitatively.

Therefore, the sample P can in particular be tested for qualitatively and/or quantitatively determining at least one analyte, for example in order for it to be possible to detect or identify a disease and/or pathogen or to determine other values or substances, which are important for diagnostics, for example.

Particularly preferably, a molecular-biological test is made possible by means of the analysis system 1 and/or analysis device 200 and/or by means of the cartridge 100.

Particularly preferably, a nucleic-acid assay is made possible or carried out in order to detect or identify a target nucleic-acid sequence ZN, in particular a target DNA sequence and/or target RNA sequence. However, it may also be provided that further assays, such as a protein assay and/or an aptamer assay, are additionally carried out.

Preferably, the sample P or individual components of the sample P or analytes can be amplified if necessary, in particular by means of PCR, and can be tested, identified and/or detected in the analysis system 1 or analysis device 200 or in the cartridge 100, and/or for the purpose of carrying out the nucleic-acid assay. Preferably, amplification products of the analyte or analytes are thus produced.

In the following, further details are first given on a preferred construction of the cartridge 100, with features of the cartridge 100 preferably also directly representing features of the analysis system 1, in particular even without any further explicit explanation.

The cartridge 100 is preferably at least substantially planar, flat plate-shaped and/or card-like.

The cartridge 100 preferably comprises an in particular at least substantially planar, flat, plate-shaped and/or card-like main body or support 101, the main body or support 101 in particular being made of and/or injection-molded from plastics material, particularly preferably polypropylene.

The cartridge 100 preferably comprises at least one film or cover 102 for covering the main body 101 and/or cavities and/or channels formed therein at least in part, in particular on the front 100A, and/or for forming valves or the like, as shown by dashed lines in FIG. 2.

The analysis system 1 or cartridge 100 or the main body 101 thereof, in particular together with the cover 102, preferably forms and/or comprises a fluidic system 103, referred to in the following as the fluid system 103.

The cartridge 100, the main body 101 and/or the fluid system 103 are preferably at least substantially vertically oriented in the operating position and/or during the test, in particular in the analysis device 200, as shown schematically in FIG. 1. In particular, the main plane or surface extension of the cartridge 100 thus extends at least substantially vertically in the operating position.

The cartridge 100 and/or the fluid system 103 preferably comprises a plurality of cavities, in particular at least one receiving cavity 104, at least one metering cavity 105, at least one intermediate cavity 106, at least one mixing cavity 107, at least one storage cavity 108, at least one reaction cavity 109, at least one intermediate temperature-control cavity 110 and/or at least one collection cavity 111, a plurality of cavities preferably being fluidically interconnected in particular by a plurality of channels 114.

Within the meaning of the present invention, channels are preferably elongate forms for conducting a fluid in a main flow direction, the forms preferably being closed transversely, in particular perpendicularly, to the main flow direction and/or longitudinal extension, preferably on all sides.

In particular, the main body or support 101 comprises elongate notches, recesses, depressions or the like, which are closed at the sides by the cover 102 and form channels within the meaning of the present invention.

Within the meaning of the present invention, cavities or chambers are preferably formed by recesses, depressions or the like in the cartridge 100 or support or main body 101, which are closed or covered by the cover 102, in particular at the sides. The space enclosed by each cavity is preferably fluidically linked by means of channels.

In particular, within the meaning of the present invention, a cavity comprises at least two openings for the inflow and/or outflow of fluids.

Within the meaning of the present invention, cavities preferably have a larger diameter and/or flow cross section than channels, preferably by at least a factor of 2, 3 or 4. In principle, however, cavities may in some cases also be elongate, in a similar manner to channels.

The cartridge 100 and/or the fluid system 103 also preferably comprises at least one pump apparatus 112 and/or at least one sensor arrangement or sensor apparatus 113. In particular, the sensor apparatus 113 forms part of a sensor arrangement, as shown in FIG. 6 and FIG. 8 to 11.

In the example shown, the cartridge 100 or the fluid system 103 preferably comprises two metering cavities 105A and 105B, a plurality of intermediate cavities 106A to 106G, a plurality of storage cavities 108A to 108E and/or a plurality of reaction cavities 109, which can preferably be loaded separately from one another, in particular a first reaction cavity 109A, a second reaction cavity 109B and an optional third reaction cavity 109C, as can be seen in FIG. 2.

The metering cavities 105 are preferably designed to receive, to temporarily store and/or to meter the sample P, and/or to pass on said sample in a metered manner. Particularly preferably, the metering cavities 105 have a diameter which is larger than that of the (adjacent) channels.

In the initial state of the cartridge 100 or when at the factory, the storage cavities 108 are preferably filled at least in part, in particular with a liquid such as a reagent, solvent or wash buffer.

The collection cavity 111 is preferably designed to receive larger quantities of fluids that are in particular used for the test, such as sample residues or the like. Preferably, in the initial state or when at the factory, the collection cavity 111 is empty or filled with gas, in particular air. The volume of the collection cavity 111 corresponds to or preferably exceeds the (cumulative) volume of the storage cavity/cavities 108 or the liquid content thereof and/or the volume of the receiving cavity 104 or the sample P received.

The reaction cavity/cavities 109 is/are preferably designed to allow a substance located in the reaction cavity 109 to react when an assay is being carried out, for example by being linked or coupled thermally, electrically, mechanically and/or pneumatically to apparatuses or modules of the analysis device 200.

The reaction cavity/cavities 109 is/are used in particular to carry out an amplification reaction, in particular PCR, or several, preferably different, amplification reactions, in particular PCRs. It is preferable to carry out several, preferably different, PCRs, i.e., PCRs having different primer combinations or primer pairs, in parallel and/or separately and/or in different reaction cavities 109.

To carry out the nucleic-acid assay, preferably target nucleic-acid sequences ZN, as analytes of the sample P, are amplified in the reaction cavity/cavities 109 by means of an amplification reaction, in particular in order to produce amplification products for the subsequent detection in the sensor arrangement or sensor apparatus 113.

Within the meaning of the present invention, amplification reactions are in particular molecular-biological reactions in which an analyte, in particular a target nucleic-acid sequence ZN, is amplified/copied and/or in which amplification products, in particular nucleic-acid products, of an analyte are produced. Particularly preferably, PCRs are amplification reactions within the meaning of the present invention.

"PCR" stands for polymerase chain reaction and is a molecular-biological method by means of which certain analytes, in particular portions of RNA or RNA sequences or DNA or DNA sequences, of a sample P are amplified, preferably in several cycles, using polymerases or enzymes, in particular in order to then test and/or detect the amplification products or nucleic-acid products. If RNA is intended to be tested and/or amplified, before the PCR is carried out, a cDNA is produced starting from the RNA, in particular using reverse transcriptase. The cDNA is used as a template for the subsequent PCR.

Preferably, during a PCR, a sample P is first denatured by the addition of heat in order to separate the strands of DNA or cDNA. Preferably, primers or nucleotides are then deposited on the individual separated strands of DNA or cDNA, and a desired DNA or cDNA sequence is replicated by means of polymerase and/or the missing strand is replaced by means of polymerase. This process is preferably repeated in a plurality of cycles until the desired quantity of the DNA or cDNA sequence is available.

For the PCR, non-marker primers are preferably used, i.e., primers which do not produce a marker or a label L on the amplified analyte or analytes or amplification product. As already mentioned previously, in the context of the present invention, a label is understood to mean a molecule, molecule fragment or atom which forms part of the capture molecule or is bonded thereto, and which can be specifically detected chemically and/or physically. For details regarding preferred embodiments in respect of the label, reference can be made to the above explanations in the general part of the description so as to avoid unnecessary repetition, which explanations also apply to the preferred embodiments depicted in the figures.

The amplification products, target nucleic-acid sequences ZN and/or other portions of the sample P produced in the one or more reaction cavities 109 can be conducted or fed to the connected sensor arrangement or sensor apparatus 113, in particular by means of the pump apparatus 112.

The sensor arrangement or sensor apparatus 113 is used in particular for detecting, particularly preferably qualitatively and/or quantitatively determining, the analyte or analytes of the sample P, particularly preferably the target nucleic-acid sequences ZN, or optionally also further analytes, such as target proteins or also hormones, if the sensor apparatus has been equipped with the corresponding capture molecules. Alternatively, or additionally, however, other values may also be collected and/or determined.

In particular, the pump apparatus 112 comprises or forms a tube-like or bead-like raised portion, in particular by means of the film or cover 102, particularly preferably on the back of the cartridge 100, as shown schematically in FIG. 1.

The cartridge 100, the main body 101 and/or the fluid system 103 preferably comprise a plurality of channels 114 and/or valves 115, as shown in FIG. 2.

By means of the channels 114 and/or valves 115, the cavities 104 to 111, the pump apparatus 112 and/or the sensor arrangement or sensor apparatus 113 can be temporarily and/or permanently fluidically interconnected and/or fluidically separated from one another, as required and/or optionally or selectively, in particular such that they are controlled by the analysis system 1 or the analysis device 200.

The cavities 104 to 111 are preferably each fluidically linked or interconnected by a plurality of channels 114. Particularly preferably, each cavity is linked or connected by at least two associated channels 114, in order to make it possible for fluid to fill, flow through and/or drain from the respective cavities as required.

The fluid transport or the fluid system 103 is preferably not based on capillary forces, or is not exclusively based on said forces, but in particular is essentially based on the effects of gravity and/or pumping forces and/or compressive forces and/or suction forces that arise, which are particularly preferably generated by the pump or pump apparatus 112. In this case, the flows of fluid or the fluid transport and the metering are controlled by accordingly opening and closing the valves 115 and/or by accordingly operating the pump or pump apparatus 112, in particular by means of a pump drive 202 of the analysis device 200.

Preferably, each of the cavities 104 to 110 has an inlet at the top and an outlet at the bottom in the operating position. Therefore, if required, only liquid from the respective cavities can be removed via the outlet.

In the operating position, the liquids from the respective cavities are preferably removed, in particular drawn out, via the outlet that is at the bottom in each case, it preferably being possible for gas or air to flow and/or be pumped into the respective cavities via the inlet that is in particular at the top. In particular, relevant vacuums in the cavities can thus be prevented or at least minimized when conveying the liquids.

In particular, the cavities, particularly preferably the storage cavity/cavities 108, the mixing cavity 107 and/or the receiving cavity 104, are each dimensioned and/or oriented in the normal operating position such that, when said cavities are filled with liquid, bubbles of gas or air that may potentially form rise upwards in the operating position, such that the liquid collects above the outlet without bubbles. However, other solutions are also possible here.

The receiving cavity 104 preferably comprises a connection 104A for introducing the sample P. In particular, the sample P may for example be introduced into the receiving cavity 104 and/or cartridge 100 via the connection 104A by means of a pipette, syringe or other instrument.

The receiving cavity 104 preferably comprises an inlet 104B, an outlet 104C and an optional intermediate connection 104D, it preferably being possible for the sample P or a portion thereof to be removed and/or conveyed further via the outlet 104C and/or the optional intermediate connection 104D. Gas, air or another fluid can flow in and/or be pumped in via the inlet 104B, as already explained.

Preferably, the sample P or a portion thereof can be removed, optionally and/or depending on the assay to be carried out, via the outlet 104C or the optional intermediate connection 104D of the receiving cavity 104. In particular, a supernatant of the sample P, such as blood plasma or blood serum, can be conducted away, discharged or removed via the optional intermediate connection 104D, in particular for carrying out the protein assay, for example.

Preferably, at least one valve 115 is assigned to each cavity and/or storage cavity 108, the receiving cavity 104, the pump apparatus 112 and/or the sensor apparatus 113 and/or is arranged upstream of the respective inlets and/or downstream of the respective outlets.

Preferably, the cavities 104 to 111 or sequences of cavities 104 to 111, through which fluid flows in series or in succession for example, can be selectively released and/or fluid can selectively flow therethrough by the assigned valves 115 being actuated, and/or said cavities can be fluidically connected to the fluid system 103 and/or to other cavities.

In particular, the valves 115 are formed by the main body 101 and the film or cover 102 and/or are formed therewith and/or are formed in another manner, for example by or having additional layers, depressions or the like.

Particularly preferably, one or more valves 115A are provided which are preferably tightly closed initially or in the storage state, particularly preferably in order to seal liquids or liquid reagents F, located in the storage cavities 108, and/or the fluid system 103 from the open receiving cavity 104 in a storage-stable manner.

Preferably, an initially closed valve 115A is arranged upstream and downstream of each storage cavity 108. Said valves are preferably only opened, in particular automatically, when the cartridge 100 is actually being used and/or during or after inserting the cartridge 100 into the analysis device 200 and/or for carrying out the assay.

A plurality of valves 115A, in particular three valves in this case, are preferably assigned to the receiving cavity 104, in particular if the intermediate connection 104D is provided in addition to the inlet 104B and the outlet 104C. Depending on the use, in addition to the valve 115A on the inlet 104B, then preferably only the valve 115A either at the outlet 104C or at the intermediate connection 104D is opened.

The valves 115A assigned to the receiving cavity 104 seal the fluid system 103 and/or the cartridge 100 in particular fluidically and/or in a gas-tight manner, preferably until the sample P is inserted and/or the receiving cavity 104 or the connection 104A of the receiving cavity 104 is closed.

As an alternative or in addition to the valves 115A (which are initially closed), one or more valves 115B are preferably provided which are not closed in a storage-stable manner and/or which are open initially or in an inoperative position, in an initial state or when the cartridge 100 is not inserted into the analysis device 200, and/or which can be closed by actuation. These valves 115B are used in particular to control the flows of fluid during the test.

The cartridge 100 is preferably designed as a microfluidic card and/or the fluid system 103 is preferably designed as a microfluidic system. In the present invention, the term "microfluidic" is preferably understood to mean that the respective volumes of individual cavities, some of the cavities or all of the cavities 104 to 111 and/or channels 114 are, separately or cumulatively, less than 5 ml or 2 ml, particularly preferably less than 1 ml or 800 µl, in particular less than 600 µl or 300 µl, more particularly preferably less than 200 µl or 100 µl.

Particularly preferably, a sample P having a maximum volume of 5 ml, 2 ml or 1 ml can be introduced into the cartridge 100 and/or the fluid system 103, in particular the receiving cavity 104.

Reagents and liquids which are preferably introduced or provided before the test in liquid form as liquids or liquid reagents F and/or in dry form as dry reagents S are required for testing the sample P, as indicated in the schematic view according to FIG. 2 by reference signs F1 to F5 and S1 to S10.

Furthermore, other liquids F, in particular in the form of a wash buffer, solvent for dry reagents S and/or a substrate SU, for example in order to form detector molecules D and/or a redox system, are also preferably required for the test, the detection process and/or for other purposes and are in particular provided in the cartridge 100, i.e., are likewise introduced before use, in particular before delivery. At some points in the following, a distinction is not made between liquid reagents and other liquids, and therefore the respective explanations are accordingly also mutually applicable.

The analysis system 1 or the cartridge 100 preferably contains all the reagents and liquids required for pretreating the sample P and/or for carrying out the test or assay, in particular for carrying out one or more amplification reactions or PCRs, and therefore, particularly preferably, it is only necessary to receive the optionally pretreated sample P.

The cartridge 100 or the fluid system 103 preferably comprises a bypass 114A that can optionally be used, in order for it to be possible, if necessary, to conduct or convey the sample P or components thereof past the reaction cavities 109 and/or, by bypassing the optional intermediate temperature-control cavity 110, also directly to the sensor apparatus 113.

Preferably, the bypass 114A is used when additionally carrying out a protein assay, in particular in order to feed the sample P or a portion thereof directly from the mixing cavity 107 to the sensor arrangement or sensor apparatus 113, and/or to conduct said sample or portion past the reaction cavities 109 and/or the intermediate temperature-control cavity 110.

The cartridge 100 or the fluid system 103 or the channels 114 preferably comprise sensor portions 116 or other apparatuses for detecting liquid fronts and/or flows of fluid.

It is to be noted that various components, such as the channels 114, the valves 115, in particular the valves 115A that are initially closed and the valves 115B that are initially open, and the sensor portions 116 in FIG. 2 are, for reasons of clarity, only labelled in some cases, but the same symbols are used in FIG. 2 for each of these components.

The collection cavity 111 is preferably used for receiving excess or used reagents and liquids and volumes of the sample, and/or for providing gas or air in order to empty individual cavities and/or channels. In the initial state, the collection cavity 111 is preferably filled solely with gas, in particular air.

In particular, the collection cavity 111 can optionally be connected to individual cavities and channels or other apparatuses fluidically in order to remove reagents and liquids from said cavities, channels or other apparatuses and/or to replace said reagents and liquids with gas or air. The collection cavity 111 is preferably given appropriate (large) dimensions.

Once the sample P has been introduced into the receiving cavity 104 and the connection 104A has been closed, the cartridge 100 can be inserted into and/or received in the proposed analysis device 200 in order to test the sample P, as shown in FIG. 1. Alternatively, the sample P could also be fed in later.

FIG. 1 shows the analysis system 1 in a ready-to-use state for carrying out a test or assay on the sample P received in the cartridge 100. In this state, the cartridge 100 is therefore linked to, received by and/or inserted into the analysis device 200.

In the following, some features and aspects of the analysis device 200 are first explained in greater detail, in particular on the basis of FIG. 1. The features and aspects relating to said device are preferably also directly features and aspects of the proposed analysis system 1, in particular even without any further explicit explanation.

The analysis system 1 or analysis device 200 preferably comprises a mount or receptacle 201 for mounting and/or receiving the cartridge 100.

Preferably, the cartridge 100 is fluidically, in particular hydraulically, separated or isolated from the analysis device 200. In particular, the cartridge 100 forms a preferably independent and in particular closed or sealed fluidic or hydraulic system 103 for the sample P and the reagents and other liquids. In this way, the analysis device 200 does not come into direct contact with the sample P and can in particular be reused for another test without being disinfected and/or cleaned first.

However, the analysis device 200 is preferably connected or coupled mechanically, electrically, thermally and/or pneumatically to the cartridge 100.

In particular, the analysis device 200 is designed to have a mechanical effect, in particular for actuating the pump apparatus 112 and/or the valves 115, and/or to have a thermal effect, in particular for temperature-controlling the reaction cavity/cavities 109 and/or the intermediate temperature-control cavity 110 and/or the sensor apparatus 113.

In addition, the analysis device 200 can preferably be pneumatically connected to the cartridge 100, in particular in order to actuate individual apparatuses, and/or can be electrically connected to the cartridge 100, in particular in order to collect and/or transmit measured values, for example from the sensor apparatus 113 and/or sensor portions 116.

The analysis system 1 or analysis device 200 preferably comprises a pump drive 202, the pump drive 202 in particular being designed for mechanically actuating the pump apparatus 112.

Preferably, a head of the pump drive 202 can be rotated in order to rotationally axially depress the preferably bead-like raised portion of the pump apparatus 112. Particularly preferably, the pump drive 202 and pump apparatus 112 together form a pump, in particular in the manner of a hose pump or peristaltic pump and/or a metering pump, for the fluid system 103 and/or the cartridge 100.

Particularly preferably, the pump is constructed as described in DE 10 2011 015 184 B4. However, other structural solutions are also possible.

Preferably, the capacity and/or discharge rate of the pump can be controlled and/or the conveying direction of the pump and/or pump drive 202 can be switched. Preferably, fluid can thus be pumped forwards or backwards as desired.

The analysis system 1 or analysis device 200 preferably comprises a connection apparatus 203 for in particular electrically and/or thermally connecting the cartridge 100 and/or the sensor arrangement or sensor apparatus 113.

As shown in FIG. 1, the connection apparatus 203 preferably comprises a plurality of electrical contact elements 203A, the cartridge 100, in particular the sensor arrangement or sensor apparatus 113, preferably being electrically connected or connectable to the analysis device 200 by the contact elements 203A. The contact elements 203A are preferably contact springs; however, they may also be spring-loaded connector pins or the like.

The analysis system 1 or analysis device 200 preferably comprises one or more temperature-control apparatuses 204 for temperature-controlling the cartridge 100 and/or having a thermal effect on the cartridge, in particular for heating and/or cooling, the temperature-control apparatus(es) 204 (each) preferably comprising or being formed by a heating resistor or a Peltier element.

Individual temperature-control apparatuses 204, some of these apparatuses or all of these apparatuses can preferably be positioned against the cartridge 100, the main body 101, the cover 102, the sensor arrangement, sensor apparatus 113 and/or individual cavities and/or can be thermally coupled thereto and/or can be integrated therein and/or in particular can be operated or controlled electrically by the analysis device 200. In the example shown, in particular the temperature-control apparatuses 204A, 204B and/or 204C are provided.

Preferably, the temperature-control apparatus 204A, referred to in the following as the reaction temperature-control apparatus 204A, is assigned to the reaction cavity 109 or to a plurality of reaction cavities 109, in particular in order for it to be possible to carry out one or more amplification reactions therein.

When the cartridge 100 is inserted, the reaction temperature-control apparatus 204A preferably abuts the cartridge 100 in the region of the reaction cavity/cavities 109, and therefore a fluid located in said cartridge, in particular the sample P, can be heated and/or cooled.

The reaction cavities 109 are preferably temperature-controlled simultaneously and/or uniformly, in particular by means of one common reaction temperature-control apparatus 204A or two reaction temperature-control apparatuses 204A.

Alternatively, each reaction cavity 109 can be temperature-controlled independently and/or individually.

More particularly preferably, the reaction cavity/cavities 109 can be temperature-controlled from two different sides and/or by means of two or the reaction temperature-control apparatuses 204A that are preferably arranged on opposite sides.

The temperature-control apparatus 204B, referred to in the following as the intermediate temperature-control apparatus 204B, is preferably assigned to the intermediate temperature-control cavity 110 and/or is designed to (actively)

temperature-control or heat the intermediate temperature-control cavity 110 or a fluid located therein, in particular the analytes, amplification products and/or target nucleic-acid sequences ZN, preferably to a preheat temperature, denaturing temperature and/or melting point or melting temperature.

The intermediate temperature-control cavity 110 and/or intermediate temperature-control apparatus 204B is preferably arranged upstream of or (immediately) before the sensor arrangement or sensor apparatus 113, in particular in order for it to be possible to temperature-control or preheat, in a desired manner, fluids to be fed to the sensor arrangement or sensor apparatus 113, in particular analytes, amplification products and/or target nucleic-acid sequences ZN, particularly preferably immediately before said fluids are fed.

Particularly preferably, the intermediate temperature-control cavity 110 or intermediate temperature-control apparatus 204B is designed or intended to denature the sample P, analytes, the produced amplification products and/or target nucleic-acid sequences ZN, and/or to divide and/or melt any double-stranded analytes, amplification products and/or target nucleic-acid sequences ZN into single strands and/or to counteract premature bonding or hybridizing of the amplification products and/or target nucleic-acid sequences ZN, in particular by the addition of heat. Furthermore, the temperature of the fluids to be fed to the sensor apparatus 113 is preferably set or adjusted by means of the intermediate temperature-control apparatus 204B such that capture molecules, in particular hairpin probes HS, arranged on the sensor apparatus 113, in particular on the sensor fields 113A, are denatured in order to provide for hybridization to the target nucleic-acid sequences. However, it is preferably possible for the sensor apparatus 113 to be temperature-controlled separately, as described below, in particular by means of a sensor temperature-control apparatus 204C.

Preferably, the analysis system 1, analysis device 200 and/or the cartridge 100 and/or one or each temperature-control apparatus 204 comprise/comprises a temperature detector and/or temperature sensor (not shown), in particular in order to make it possible to control and/or feedback control the temperature.

One or more temperature sensors may for example be assigned to the sensor portions 116 and/or to individual channel portions or cavities, i.e., may be thermally coupled thereto.

The temperature-control apparatus 204C, referred to in the following as the sensor temperature-control apparatus 204C, is in particular assigned to the sensor apparatus 113 and/or is designed to (actively) temperature-control or heat fluids located in or on the sensor arrangement or sensor apparatus 113, in particular analytes or target nucleic-acid sequences ZN, in a desired manner, in particular in order to bond and/or denature said fluids. The temperature-control apparatus 204C is used in particular, specifically when a fluid is being transferred to the sensor apparatus 113, to denature capture molecules, in particular hairpin probes HS, and to set optimum temperatures for hybridization to the target analytes.

The temperature-control apparatus 204C can preferably be formed such that the temperature of the sensor arrangement or sensor apparatus 113 can be (feedback) controlled in the form of a special temperature regime, such as a gradient, in particular a decreasing temperature gradient. Preferably, during or after the introduction of the fluid into the sensor arrangement or sensor apparatus 113, the temperature of the sensor arrangement or sensor apparatus is set or adjusted in the range of from 90 to 100° C. in order to denature the capture molecules and is then reduced to values in the range of from 50 to 60° C. such that the range of usually preferred hybridization temperatures is run through.

The sensor temperature-control apparatus 204C is preferably planar and/or has a contact surface which is preferably rectangular and/or corresponds to the dimensions of the sensor arrangement or sensor apparatus 113, the contact surface allowing for heat transfer between the sensor temperature-control apparatus 204C and the sensor apparatus 113.

Preferably, the analysis device 200 comprises the sensor temperature-control apparatus 204C. However, other structural solutions are also possible in which the sensor temperature-control apparatus 204C is integrated in the cartridge 100, in particular the sensor arrangement or sensor apparatus 113.

Particularly preferably, the connection apparatus 203 comprises the sensor temperature-control apparatus 204C, and/or the connection apparatus 203 together with the sensor temperature-control apparatus 204C can be linked to, in particular pressed against, the cartridge 100, in particular the sensor arrangement or sensor apparatus 113.

More particularly preferably, the connection apparatus 203 and the sensor temperature-control apparatus 204C (together) can be moved towards and/or relative to the cartridge 100, in particular the sensor arrangement or sensor apparatus 113, and/or can be positioned against or abutted on said cartridge, preferably in order to both electrically and thermally couple the analysis device 200 to the cartridge 100, in particular the sensor arrangement or sensor apparatus 113 or the support 113D thereof.

Preferably, the sensor temperature-control apparatus 204C is arranged centrally on the connection apparatus 203 or a support thereof and/or is arranged between the contact elements 203A.

In particular, the contact elements 203A are arranged in an edge region of the connection apparatus 203 or a support thereof or are arranged around the sensor temperature-control apparatus 204C, preferably such that the connection apparatus 203 is connected or connectable to the sensor apparatus 113 thermally in the center and electrically on the outside or in the edge region. However, other solutions are also possible here.

The analysis system 1 or analysis device 200 preferably comprises one or more actuators 205 for actuating the valves 115. Particularly preferably, different (types or groups of) actuators 205A and 205B are provided which are assigned to the different (types or groups of) valves 115A and 115B for actuating each of said valves, respectively.

The analysis system 1 or analysis device 200 preferably comprises one or more sensors 206. In particular, fluid sensors 206A are assigned to the sensor portions 116 and/or are designed or intended to detect liquid fronts and/or flows of fluid in the fluid system 103.

Particularly preferably, the fluid sensors 206A are designed to measure or detect, in particular in a contact-free manner, for example optically and/or capacitively, a liquid front, flow of fluid and/or the presence, the speed, the mass flow rate/volume flow rate, the temperature and/or another value of a fluid in a channel and/or a cavity, in particular in a respectively assigned sensor portion 116, which is in particular formed by a planar and/or widened channel portion of the fluid system 103.

Particularly preferably, the sensor portions 116 are each oriented and/or incorporated in the fluid system 103 and/or fluid flows against or through the sensor portions 116 such that, in the operating position of the cartridge 100, fluid flows through the sensor portions 116 in the vertical direction and/or from the bottom to the top, or vice versa, in particular in order to make it possible or easier to accurately detect liquid.

Alternatively or additionally, the analysis device 200 preferably comprises (other or additional) sensors 206B for detecting the ambient temperature, internal temperature, atmospheric humidity, position, and/or alignment, for example by means of a GPS sensor, and/or the orientation and/or inclination of the analysis device 200 and/or the cartridge 100.

The analysis system 1 or analysis device 200 preferably comprises a control apparatus 207, in particular comprising an internal clock or time base for controlling the sequence of a test or assay and/or for collecting, evaluating and/or outputting or providing measured values in particular from the sensor apparatus 113, and/or from test results and/or other data or values.

The control apparatus 207 preferably controls or feedback controls the pump drive 202, the temperature-control apparatuses 204 and/or actuators 205, in particular taking into account or depending on the desired test and/or measured values from the sensor arrangement or sensor apparatus 113 and/or sensors 206.

The flows of fluid are controlled in particular by accordingly activating the pump or pump apparatus 112 and actuating the valves 115.

Particularly preferably, the pump drive 202 comprises a servomotor, stepper motor, or a drive calibrated in another way or a drive having a rotational speed and/or number of (partial) revolutions that can be controlled or feedback controlled, such that desired metering can be achieved, at least in principle, by means of appropriate activation.

Additionally or alternatively, the fluid sensors 206A are used to detect liquid fronts or flows of fluid, in particular in cooperation with the assigned sensor portions 116, in order to achieve the desired fluidic sequence and the desired metering by accordingly controlling the pump or pump apparatus 112 and accordingly activating the valves 115.

Optionally, the analysis system 1 or analysis device 200 comprises an input apparatus 208, such as a keyboard, a touch screen or the like, and/or a display apparatus 209, such as a screen.

The analysis system 1 or analysis device 200 preferably comprises at least one interface 210, for example for controlling, for communicating and/or for outputting measured data or test results and/or for linking to other devices, such as a printer, an external power supply or the like. This may in particular be a wired or wireless interface 210.

The analysis system 1 or analysis device 200 preferably comprises a power supply 211 for providing electrical power, preferably a battery or an accumulator, which is in particular integrated and/or externally connected or connectable.

Preferably, an integrated accumulator is provided as a power supply 211 and is (re)charged by an external charging device (not shown) via a connection 211A and/or is interchangeable.

The analysis system 1 or analysis device 200 preferably comprises a housing 212, all the components and/or some or all of the apparatuses preferably being integrated in the housing 212. Particularly preferably, the cartridge 100 can be inserted or slid into the housing 212, and/or can be received by the analysis device 200, through an opening 213 which can in particular be closed, such as a slot or the like.

The analysis system 1 or analysis device 200 is preferably portable or mobile. Particularly preferably, the analysis device 200 weighs less than 25 kg or 20 kg, particularly preferably less than 15 kg or 10 kg, in particular less than 9 kg or 6 kg.

As already explained, the analysis device 200 can preferably be pneumatically linked to the cartridge 100, in particular to the sensor arrangement and/or to the pump apparatus 112.

Particularly preferably, the analysis device 200 is designed to supply the cartridge 100, in particular the sensor arrangement and/or the pump apparatus 112, with a working medium, in particular gas or air.

Preferably, the working medium can be compressed and/or pressurized in the analysis device 200 or by means of the analysis device 200.

Preferably, the analysis device 200 comprises a pressurized gas supply 214, in particular a pressurized gas generator or a compressor, preferably in order to compress, condense and/or pressurize the working medium.

The pressurized gas supply 214 is preferably integrated in the analysis device 200 or the housing 212 and/or can be controlled or feedback controlled by means of the control apparatus 207.

Preferably, the pressurized gas supply 214 is electrically operated or can be operated by electrical power. In particular, the pressurized gas supply 214 can be supplied with electrical power by means of the power supply 211.

Preferably, air can be drawn in, in particular from the surroundings, as the working medium by means of the analysis device 200 or pressurized gas supply 214.

The analysis device 200 or pressurized gas supply 214 preferably comprises a connection element 214A, in particular in order to pneumatically connect the analysis device 200 or pressurized gas supply 214 to the cartridge 100.

In the following, further details are given on a preferred construction and the preferred mode of operation of the analysis system 1 and/or the cartridge 100 or the sensor arrangement, with reference to FIG. 3 to FIG. 11. The features of the sensor apparatus 113 and/or of the sensor arrangement formed thereby are preferably also directly features of the analysis system and/or of the cartridge 100, in particular even without any further explicit indication.

The sensor arrangement preferably comprises the sensor apparatus 113, a sensor cover 117 for the sensor apparatus 113, a sensor compartment 118, an inlet 119 into the sensor compartment 118 and/or an outlet 120 out of the sensor compartment 118, as shown in FIGS. 2, 6 and 8 to 11.

The sensor arrangement, in particular the sensor apparatus 113, is preferably designed for electrochemically measuring or detecting analytes of the sample P.

In particular, the sensor arrangement or sensor apparatus 113 is designed to identify, to detect and/or to determine (identical or different) analytes bonded to capture molecules or products derived therefrom, in particular amplification products of the analyte or different analytes.

The sensor arrangement is preferably designed as a multiple-part module, the sensor apparatus 113 and the sensor cover 117 preferably each forming a component of the sensor assembly or module.

Preferably, the sensor arrangement has a layered construction, the sensor apparatus 113 preferably forming a base of the sensor arrangement and the sensor cover 117 being directly connected to the sensor apparatus 113, at least at the edge, and/or resting thereon.

The sensor apparatus 113 and the sensor cover 117 define or delimit the sensor compartment 118, preferably on the flat sides. In particular, the sensor compartment 118 is formed or arranged between the sensor apparatus 113 and the sensor cover 117.

The sensor compartment 118 preferably has, in particular when the sensor cover 117 is not actuated or has been moved away, a volume of greater than 0.1 µl or 0.2 µl, particularly preferably greater than 0.5 µl or 1 µl, in particular greater than 2 µl, and/or less than 10 µl or 8 µl, particularly preferably less than 6 µl or 3 µl.

The sensor arrangement, in particular the sensor apparatus 113 and the sensor cover 117, is/are preferably planar, flat and/or plate-shaped. Preferably, the surface area of a flat side of the sensor apparatus 113 and/or sensor cover 117 is less than 400 mm$^2$ or 300 mm$^2$, particularly preferably less than 250 mm$^2$ or 150 mm$^2$, in particular less than 100 mm$^2$ or 50 mm$^2$, and/or greater than 0.01 mm$^2$ or 0.25 mm$^2$, particularly preferably greater than 1 mm$^2$ or 4 mm$^2$.

The sensor apparatus 113 preferably has a front side or measuring side and a rear side or connection side, the measuring side and the connection side each preferably forming one flat side of the in particular planar, flat and/or plate-shaped sensor apparatus 113.

The measuring side is preferably the side of the sensor apparatus 113 facing the fluid or the sample P or the analyte or the sensor compartment 118.

The connection side is preferably opposite the measuring side and/or is the side of the sensor apparatus 113 that faces away from the fluid or the sample P or the analyte or the sensor compartment 118.

The sensor apparatus 113 preferably comprises (precisely) one sensor array 113A on the measuring side, having a plurality of sensor cavities and/or sensor fields 113B, the sensor fields 113B preferably being round, in particular circular, in a plan view of the sensor array 113A and/or being arranged so as to be spatially separated from one another and/or directly next to one another.

Figure 3:
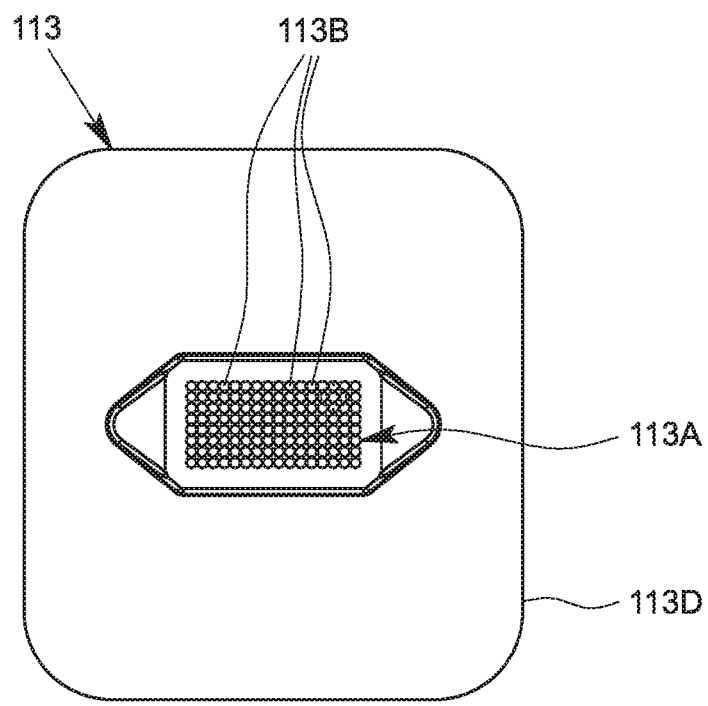
FIG. 3 is a schematic front view of a sensor apparatus of the analysis system and/or cartridge.
Figure 4:
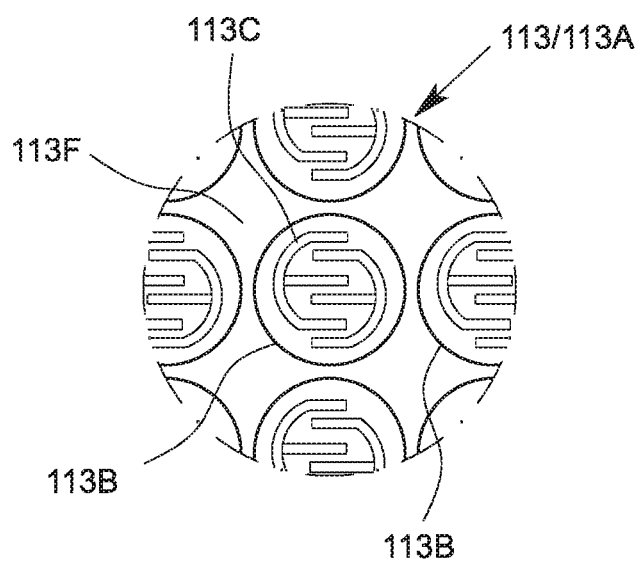
FIG. 4 is an enlarged detail from FIG. 3 illustrating a sensor Field of the sensor apparatus.
Figure 5:
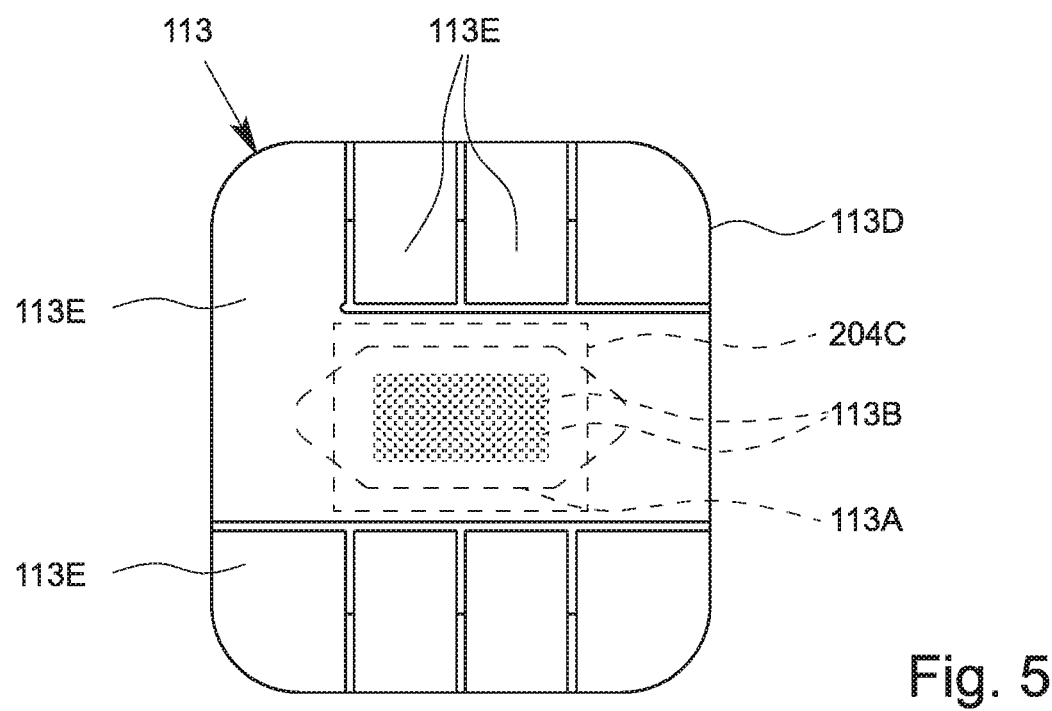
FIG. 5 is a schematic rear view of the sensor apparatus.

FIG. 3 is a plan view of the sensor array 113A or the measuring side of the sensor apparatus 113. FIG. 4 is an enlarged detail from FIG. 3. FIG. 5 shows the connection side of the sensor arrangement or the sensor apparatus 113. FIG. 6 and FIG. 8 to 11 are each schematic sections through the sensor arrangement during different method steps.

Preferably, the sensor arrangement or sensor apparatus 113 or the sensor array 113A comprises more than 10 or 20, particularly preferably more than 50 or 80, in particular more than 100 or 120 and/or less than 1000 or 800 sensor fields 113B.

Preferably, the sensor fields 113B are separated or spaced apart from one another, in particular by less than 100 µm or 10 µm and/or more than 10 nm or 100 nm. Particularly preferably, all the sensor fields 113B are arranged on a surface area of less than 100 mm$^2$ and/or greater than 1 mm$^2$ and/or the sensor array 113A has a surface area of less than 100 mm$^2$ and/or greater than 1 mm$^2$.

The sensor fields 113B are in particular spatially separated measuring regions of the sensor apparatus 113 and/or sensor array 113A that, independently from one another, allow an analyte to be detected, identified and/or measured. Different sensor fields 113B can thus detect and/or measure different analytes, respectively. However, a plurality of sensor fields 113B could also measure the same analytes, again independently from one another, depending on the capture molecules with which the sensor fields 113 are provided. Alternatively, individual sensor fields 113B can also be used for control purposes, i.e., may not be used for measuring and/or detecting an analyte.

Preferably, the sensor apparatus 113 comprises barriers or partitions between each of the sensor fields 113B, which are preferably formed by an in particular hydrophobic layer 113F having corresponding recesses for the sensor fields 113B. However, other structural solutions are also possible.

Preferably, the sensor arrangement or sensor apparatus 113 or the sensor array 113A comprises a plurality of electrodes 113C. Particularly preferably, at least two electrodes 113C are arranged in each sensor field 113B. In particular, at least or precisely two electrodes 113C corresponding to one another form one or each sensor field 113B.

The electrodes 113C are preferably made of metal, preferably so as to be electrically conductive, in particular at least the surface thereof is made of noble metal, such as platinum or gold.

Preferably, the electrodes 113C are finger-like and/or engage in one another, as can be seen from the enlarged detail of a sensor field 113B according to FIG. 4. However, other structural solutions or arrangements are also possible.

Preferably, each electrode pair forms one sensor field 113B, or each sensor field 113B contains one electrode pair.

The electrodes 113C of a sensor field 113B preferably correspond to one another in terms of their shape and size.

The sensor apparatus 113 preferably comprises a support 113D, in particular a chip comprising an electronic or integrated circuit, and/or a semiconductor chip, the electrodes 113C preferably being arranged on the support 113D and/or being integrated in the support 113D.

The sensor apparatus 113, in particular the support 113D, preferably comprises at least one, preferably a plurality of, electronic or integrated circuits, the circuits in particular being designed to detect electrical currents or voltages that are preferably generated at the sensor fields 113B in accordance with the redox cycling principle.

Particularly preferably, the measurement signals from the different sensor fields 113B are separately collected or measured by the sensor apparatus 113 and/or the circuits.

Particularly preferably, the sensor apparatus 113 and/or the integrated circuits directly convert the measurement signals into digital signals or data, which can in particular be read out by or via the analysis device 200.

Particularly preferably, the sensor apparatus 113 and/or the support 113D is constructed as described in European Patent Application EP 1 636 599 B1 and corresponding U.S. Pat. No. 7,914,655.

The sensor apparatus 113, in particular the support 113D, preferably comprises a plurality of, in this case eight, electrical contacts or contact surfaces 113E, the contacts 113E preferably being arranged on the connection side and/or forming the connection side, as shown in FIG. 5.

Preferably, the sensor apparatus 113 can be electrically contacted on the connection side and/or by means of the contacts 113E and/or can be electrically connected to the analysis device 200. In particular, an electrical connection can be established between the cartridge 100, in particular the sensor apparatus 113, and the analysis device 200, in particular the control apparatus 207, by electrically connecting the contacts 113E to the contact elements 203A of the connection apparatus 203.

Preferably, the contacts 113E are arranged laterally, in the edge region and/or in a plan view or projection around the electrodes 113C and/or the sensor array 113A, and/or the contacts 113E extend as far as the edge region of the sensor apparatus 113, in particular such that the sensor apparatus 113 can be electrically contacted, preferably by means of the connection apparatus 203 or the contact elements 203A, laterally, in the edge region and/or around the sensor temperature-control apparatus 204C, which can preferably be positioned centrally or in the middle on the support 113D, as already explained.

As already explained, the sensor compartment 118 is preferably arranged between the sensor apparatus 113 and the sensor cover 117, the measurement side and/or the sensor array 113A of the sensor apparatus 113 preferably defining or delimiting the sensor compartment 118.

Preferably, the sensor fields 113B and/or the electrodes 113C are fluidically interconnected by the sensor compartment 118, in particular such that the sensor fields 113B and/or electrodes 113C can come into contact with a fluid, the sample P and/or the analytes via the (common) sensor compartment 118.

The sensor cover 117 can preferably be moved relative to the sensor apparatus 113. In particular, the sensor cover 117 can be lowered onto the sensor apparatus 113, in particular the sensor array 113A and/or the layer 113F, preferably such that the sensor fields 113B are closed and/or fluidically separated from one another.

In particular, the fluid can be displaced out of the sensor compartment 118 by means of the sensor cover 117, and/or by lowering the sensor cover 117 onto the sensor apparatus 113.

The sensor cover 117 is therefore preferably designed to seal and/or fluidically separate the individual sensor fields 113B from one another for the actual measurement, preferably such that fluid cannot be exchanged (in a relevant manner) between the sensor fields 113B, at least when the measurement is being taken.

Figure 6:
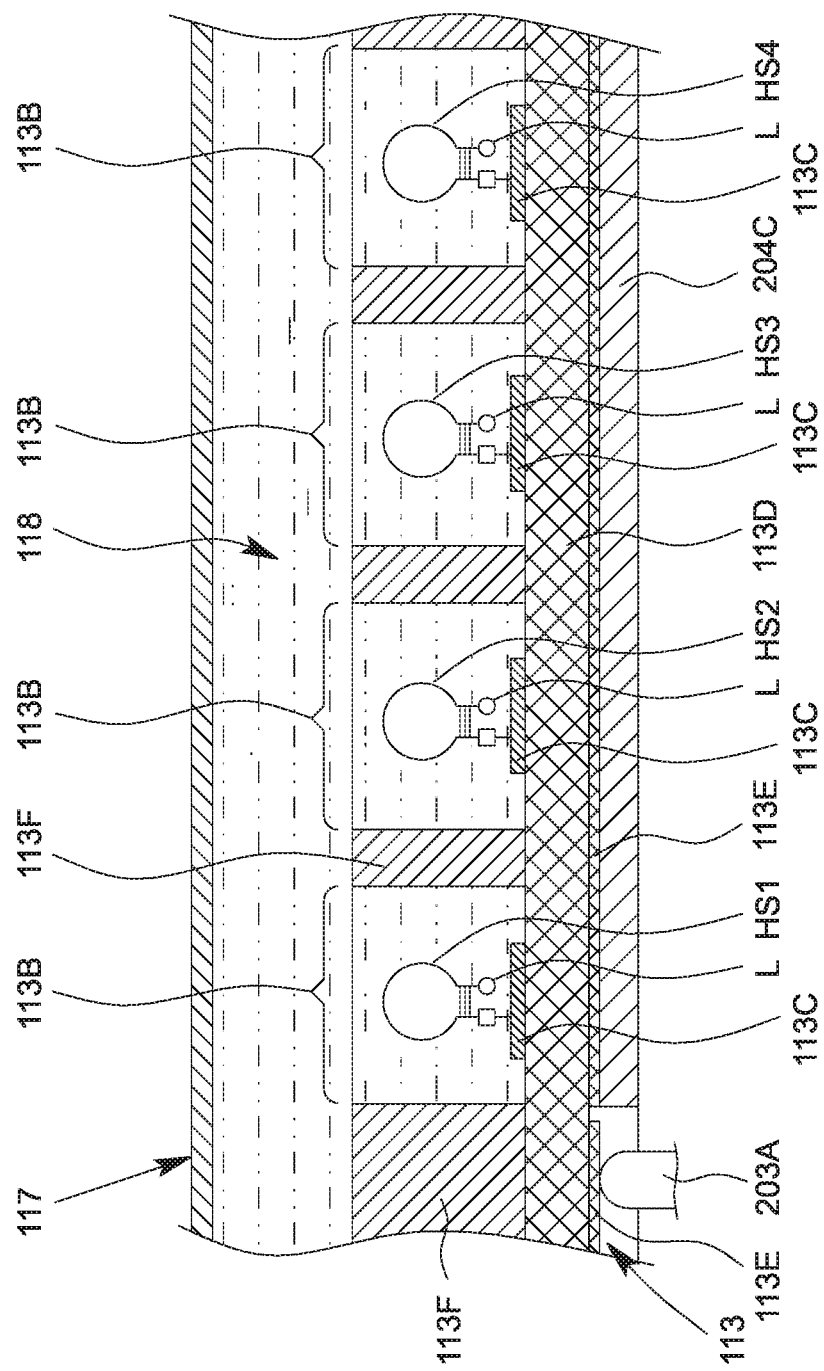
FIG. 6 is a schematic sectional view of a sensor arrangement of the analysis system and/or cartridge with the sensor apparatus and a sensor cover that has been moved away as well as hairpin probes in the closed state.
Figure 9:
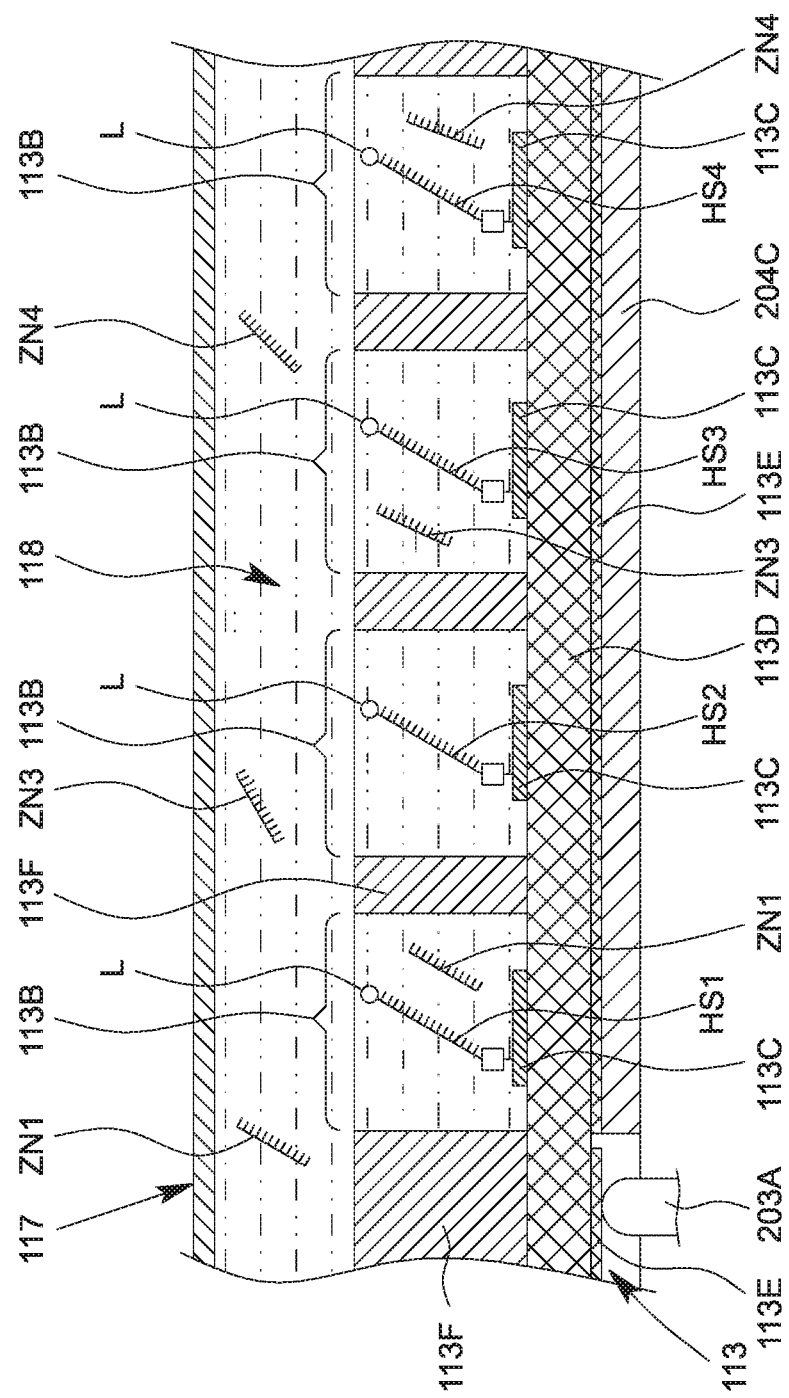
FIG. 9 is a schematic sectional view of the sensor arrangement during execution of a nucleic-acid assay with open hairpin probes.
Figure 10:
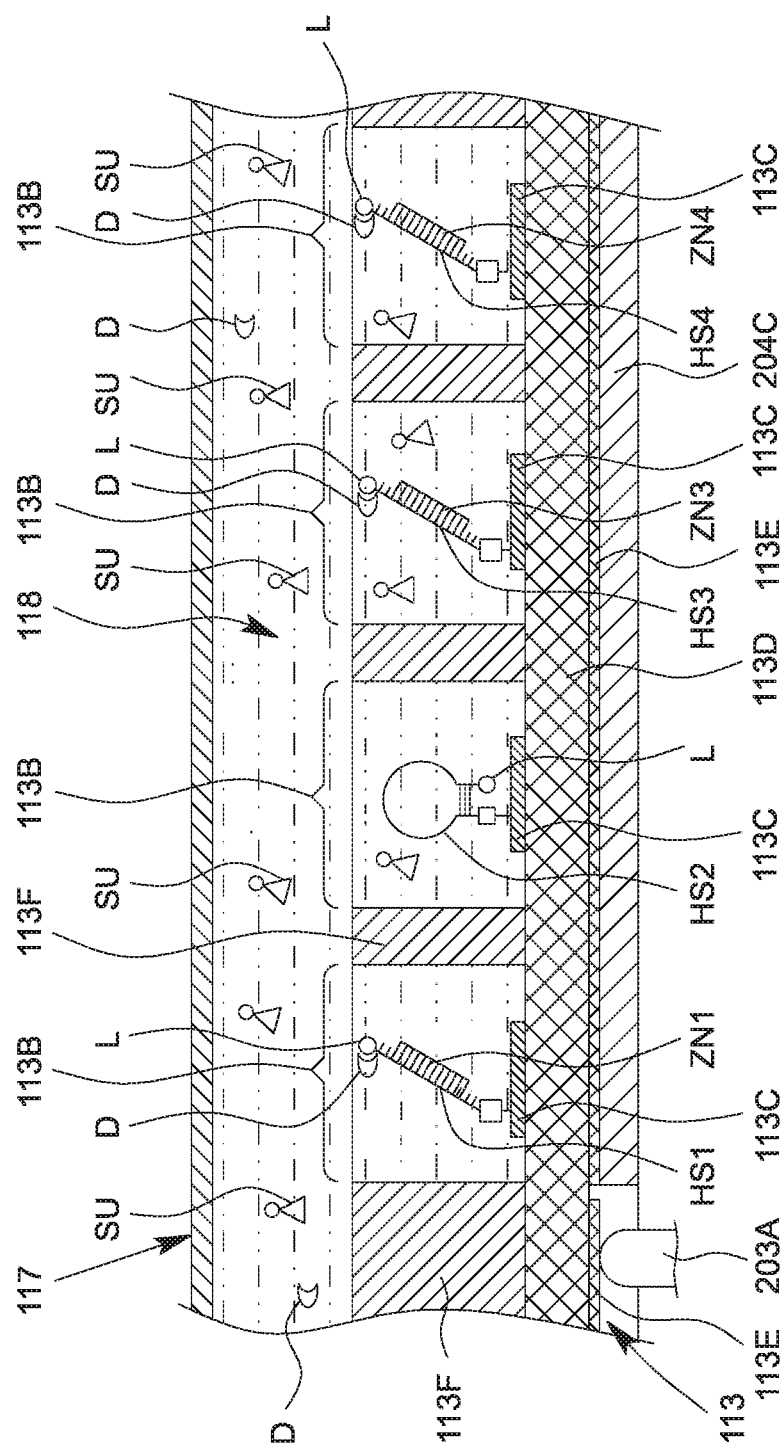
FIG. 10 is a schematic view of the sensor arrangement during execution of a nucleic-acid assay with hybridized hairpin probes.
Figure 11:
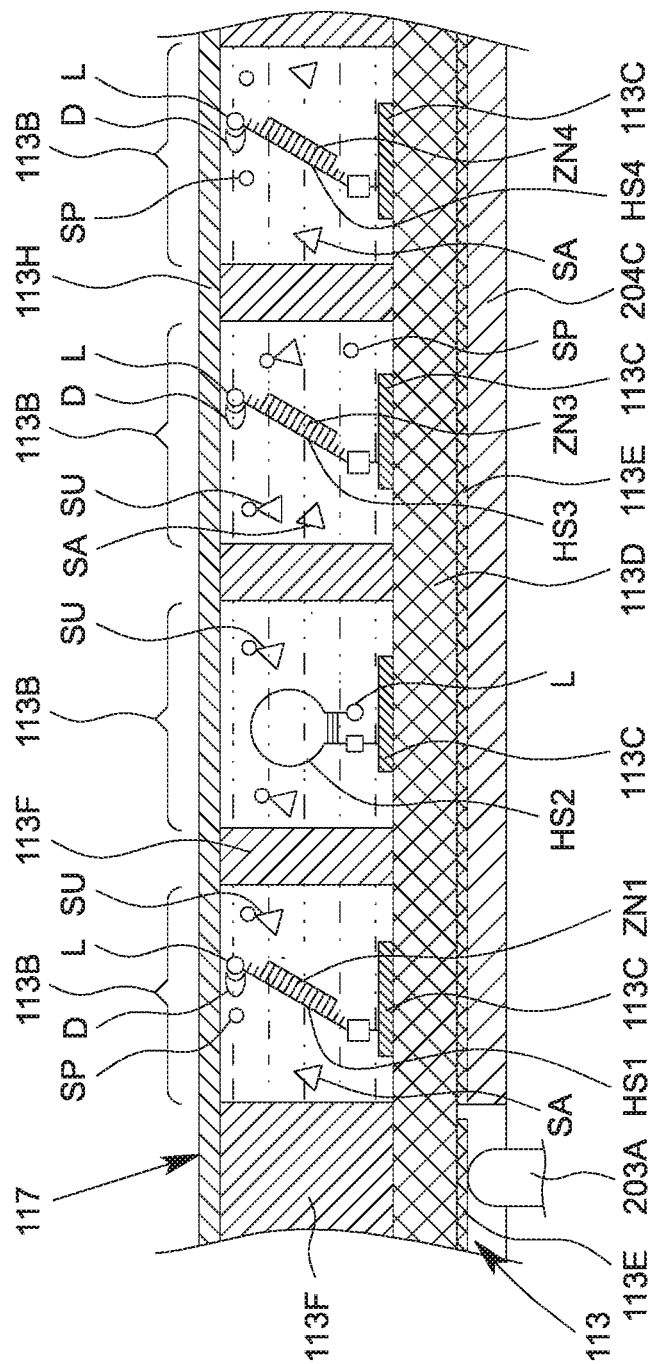
FIG. 11 is a schematic view of a sensor arrangement during execution of a nucleic-acid assay with hybridized hairpin probes after detectors and substrates have been added and with lowered sensor cover.

FIG. 6 is a schematic section through the sensor arrangement showing the sensor cover 117 moved away and capture molecules, in particular capture nucleic-acid sequences, which are in the form of hairpin probes HS in the state in which they are not capable of hybridization or the closed state. FIG. 9 is a schematic section through the sensor arrangement showing the sensor cover 117 moved away and capture molecules in the form of hairpin probes HS in the state in which they are capable of hybridization or the open state. FIG. 10 is a further schematic section through the sensor arrangement showing the sensor cover 117 moved away and capture molecules in the form of hairpin probes HS in the hybridized state. FIG. 11 is a further schematic section through the sensor arrangement showing the sensor cover 117 advanced or lowered, immediately before or during the measurement.

At least when the sensor cover 117 is moved away, the sensor apparatus 113 or the sensor compartment 118 is fluidically linked to the fluid system 103, in particular to the reaction cavity/cavities 109, preferably by the inlet 119 and the outlet 120, in particular such that fluids, in particular the (pretreated) sample P or the analytes, in particular a target nucleic-acid sequence ZN, and/or reagents, can be admitted to the measurement side of the sensor apparatus 113 or sensor array 113A.

The sensor compartment 118 can thus be loaded with fluids and/or said fluids can flow therethrough, at least when the sensor cover 117 is raised or moved away from the sensor apparatus 113 or the sensor array 113A.

Preferably, fluid can flow through the sensor compartment 118 by means of the inlet 119 and the outlet 120. In particular, a fluid can flow into the sensor compartment 118 via the inlet 119 and can flow out of the sensor compartment 118 via the outlet 120; however, the flow direction can also be reversed. In particular, the inlet 119 can function or be used as the outlet, at least temporarily, and the outlet 120 can function or be used as the inlet, at least temporarily.

The inlet 119 and/or the outlet 120 is/are preferably formed by cut-outs, holes, openings, channels or the like in the main body 101, the sensor cover 117 and/or the sensor apparatus 113.

The sensor apparatus 113 preferably comprises a plurality of in particular different capture molecules, in particular hairpin probes HS, for bonding the analytes, different capture molecules preferably being arranged and/or immobilized in or on different sensor fields 113B and/or being assigned to different sensor fields 113B.

Particularly preferably, the sensor fields 113B or electrodes 113C are provided with the capture molecules, in particular hairpin probes HS, in particular at the factory, and/or the capture molecules are immobilized or fixed in or on the sensor fields 113B or electrodes 113C, in particular at the factory.

As already explained at the outset, the capture molecules, in particular hairpin probes HS, are preferably capture nucleic-acid sequences, in particular capture DNA sequences and/or capture RNA sequences.

Different capture molecules, in particular hairpin probes, which are here illustrated by hairpin probes HS1 to HS4 by way of example, are preferably provided for the different sensor fields 113B and/or the different electrode pairs and/or electrodes 113C, in order to specifically bond different analytes, in particular target nucleic-acid sequences ZN1 to ZN4, in the sensor fields 113B.

Particularly preferably, the sensor apparatus 113 or sensor array 113A allows the analytes bonded in each sensor field 113B to be qualitatively and/or quantitatively determined.

Optionally, the sensor apparatus 113 comprises capture molecules, in particular hairpin probes HS, having different hybridization temperatures, preferably in order to bond the analytes to the corresponding capture molecules at different hybridization temperatures.

The hybridization temperature is preferably the (average) temperature at which an (amplified) analyte or a target nucleic-acid sequence ZN is bonded to a corresponding capture molecule or a corresponding capture nucleic-acid sequence FN.

The optimal hybridization temperature is preferably the temperature at which the number of analytes bonded to corresponding capture molecules is maximized and/or the number of analytes bonded to one another is minimized.

Preferably, the (optimal) hybridization temperature varies for different analytes, in particular target nucleic-acid sequences ZN.

Preferably, the temperature of the sensor apparatus 113, in particular of the electrodes 113C, the support 113D, the sensor compartment 118 and/or the sensor cover 117, can be controlled or set, at least indirectly, preferably by means of the analysis device 200, in particular by means of the temperature-control apparatus(es) 204B and/or 204C, as already explained. It is thus possible in particular for the capture molecules and the target analytes to be acted on for the purpose of denaturing.

Preferably, the sensor temperature-control apparatus 204C is used to temperature-control the sensor compartment 118, in this case by being in contact with the connection side of the sensor apparatus 113, in particular such that the desired or required or optimal denaturing temperature and/or hybridization temperature is set on the measuring side and/or in the sensor compartment 118.

In the following, a preferred sequence of a test or analysis using the proposed analysis system 1 and/or analysis device 200 and/or the proposed cartridge 100 and/or in accordance with the proposed method is explained in greater detail by way of example.

The analysis system 1, the cartridge 100 and/or the analysis device 200 is preferably designed to carry out the proposed method.

The method may be used in particular in the field of medicine, in particular veterinary medicine, for example in order to detect or identify diseases and/or pathogens. Alternatively, the method may also be used for other purposes, for example for food safety, environmental analytics or the like.

Preferably, a nucleic-acid assay is carried out in order to detect or identify a target nucleic-acid sequence ZN, in particular a target DNA sequence and/or target RNA sequence. Particularly preferably, target nucleic-acid sequences ZN are bonded as analytes of the sample P to corresponding capture molecules, in particular capture nucleic-acid sequences, preferably hairpin probes HS.

During the nucleic-acid assay, at least one analyte of the sample P is preferably amplified or copied, in particular by means of PCR.

Preferably, the bonded analytes or the amplification products thereof are electrochemically identified or detected in the assay.

At the start of the proposed method, a sample P having at least one analyte, preferably a fluid or a liquid from the human or animal body, in particular blood, saliva or urine, is preferably first introduced into the receiving cavity 104 via the connection 104A, it being possible for the sample P to be pretreated, in particular filtered.

Once the sample P has been received, the receiving cavity 104 and/or the connection 104A thereof is fluidically closed, in particular in a liquid-tight and/or gas-tight manner.

Preferably, the cartridge 100 together with the sample P is then linked to the analysis device 200, in particular is inserted or slid into the analysis device 200 or the opening 213, particularly preferably from the top.

Particularly preferably, the cartridge 100 is received, at least substantially vertically, by the analysis device 200.

The method sequence, in particular the flow and conveying of the fluids, the mixing and the like, is controlled by the analysis device 200 or the control apparatus 207, in particular by accordingly activating and actuating the pump drive 202 or the pump apparatus 112 and/or the actuators 205 or valves 115.

Preferably, the sample P or a part or supernatant of the sample P is removed from the receiving cavity 104, in particular via the outlet 104C, preferably for carrying out the nucleic-acid assay, and/or via the intermediate connection 104D, and is preferably fed to the mixing cavity 107 in a metered manner.

According to a particular embodiment of the present invention, in addition to the nucleic-acid assay, further assays, in particular protein assays and/or aptamer assays, can be carried out by means of the analysis system 1, the cartridge 100 and/or the analysis device 200. The different assays are preferably carried out sequentially such that, when the sensor fields are appropriately equipped with different capture molecules, in particular capture nucleic acids, capture proteins and/or capture aptamers, up to three analytes per sensor field can be detected or identified.

In order to carry out different assays, such as protein and/or aptamer assays, in addition to the nucleic-acid assay, the sample P is preferably split into at least two sample portions, a first sample portion being used for carrying out the protein assay and a second sample portion being used for carrying out the nucleic-acid assay. Preferably, the sample P is split into the different sample portions for the assays by being taken or removed via the outlet 104C and the intermediate connection 104D. Other variants of the method are also possible, however, in particular in which, for the assays, the sample P is split into different sample portions by being taken or removed sequentially from the mixing cavity 107.

Preferably, the sample P or a portion thereof is taken or removed for the nucleic-acid assay, selectively via the outlet 104C or the intermediate connection 104D of the receiving cavity 104, as already explained.

Preferably, the sample P or a portion thereof for the nucleic-acid assay is metered in the cartridge 100, in particular in or by means of the first metering cavity 105A and/or second metering cavity 105B, before being introduced into the mixing cavity 107. Here, in particular the upstream and/or downstream sensor portions 116 are used together with the assigned sensors 206 in order to make possible the desired metering.

After the metering, a sample portion for the nucleic-acid assay is present in the mixing cavity 107.

In the mixing cavity 107, the sample P or sample portion for the nucleic-acid assay is preferably prepared for further analysis and/or is mixed with a reagent, preferably with a liquid reagent F1 from a first storage cavity 108A and/or with one or more dry reagents S1, S2 and/or S3, which are optionally provided in the mixing cavity 107.

The liquid and/or dry reagents can be introduced into the mixing cavity 107 before and/or after the sample P. In the example shown, the dry reagents S1 to S3 are preferably introduced into the mixing cavity 107 previously and are optionally dissolved by the sample P and/or the liquid reagent F1.

The liquid reagent F1 may be a reagent, in particular a PCR master mix for the amplification reaction or PCR, and/or may be a sample buffer. Preferably, the PCR master mix contains nuclease-free water, enzymes for carrying out the PCR, in particular at least one DNA polymerase, nucleoside triphosphates (NTPs), in particular deoxynucleotides (dNTPs), salts, in particular magnesium chloride, and/or reaction buffers.

The dry reagents S1, S2 and/or S3 may likewise be reagents required for carrying out an amplification reaction or PCR, which are in a dry, in particular lyophilized, form. Preferably, the dry reagents S1, S2 and/or S3 are selected in particular from lyophilized enzymes, preferably DNA polymerases, NTPs, dNTPs and/or salts, preferably magnesium chloride.

The dissolving or mixing in the mixing cavity 107 takes place or is assisted in particular by introducing and/or blowing in gas or air, in particular from the bottom. This is carried out in particular by accordingly pumping gas or air in the circuit by means of the pump or pump apparatus 112.

Subsequently, a desired volume of the sample P that is mixed and/or pretreated in the mixing cavity 107 is preferably fed to one or more reaction cavities 109, particularly preferably via (respectively) one of the, optional intermediate cavities 106A to 106C arranged before or upstream of the respective reaction cavities 109 and/or with different reagents or primers, here dry reagents S4 to S6, being added or dissolved.

During the nucleic-acid assay the sample P or a portion thereof is removed from the mixing cavity 107 and fed to the sensor arrangement and/or sensor apparatus 113 via the reaction cavities 109 and/or the intermediate temperature-control cavity 110.

Particularly preferably, the (premixed) sample P is split into several sample portions, preferably of equal size, and/or is divided between the intermediate cavities 106A to 106C and/or reaction cavities 109, preferably evenly and/or in sample portions of equal size.

Different reagents, in the present case dry reagents S4 to S6, particularly preferably primers, in particular those required for the PCR or PCRs, in particular groups of different primers in this case, are preferably added to the (premixed) sample P or the sample portions in the intermediate cavities 106A to 106C and/or different reaction cavities 109, respectively.

The primers in the different groups or sample portions differ in particular in terms of the hybridization temperatures of the amplification products generated by the respective primers.

In the embodiment shown, the reagents or primers S4 to S6 are contained in the intermediate cavities 106A to 106C. However, other solutions are also possible, in particular those in which the reagents or primers S4 to S6 are contained in the reaction cavities 109.

According to a preferred embodiment, the intermediate cavities 106A to 106C each contain primers for amplifying/copying one analyte, preferably two different analytes and more preferably three different analytes. However, it is also possible for four or more different analytes to be amplified/copied per reaction cavity 109 or sample portion.

Particularly preferably, the reaction cavities 109 are filled in succession with a specified volume of the (pretreated) sample P or with respective sample portions via the intermediate cavities 106A to 106C that are each arranged upstream of the respective reaction cavities 109. For example, the first reaction cavity 109A is filled with a specified volume of the pretreated sample P before the second reaction cavity 109B and/or the second reaction cavity 109B is filled therewith before the third reaction cavity 109C.

In the reaction cavities 109, the amplification reactions or PCRs are carried out to copy/amplify the analytes or target nucleic-acid sequences ZN. This is carried out in particular by means of the assigned, preferably common, reaction temperature-control apparatus 204A and/or preferably simultaneously for all the reaction cavities 109, i.e., in particular using the same cycles and/or temperature (curves/profiles).

The PCR or PCRs are carried out on the basis of protocols or temperature profiles that are essentially known to a person skilled in the art. In particular, the mixture or sample volume located in the reaction cavities 109 is preferably cyclically heated and cooled.

Preferably, nucleic-acid products and/or target nucleic-acid sequences ZN are produced from the analytes as amplification products in the reaction cavity/cavities 109.

Particularly preferably, during the nucleic-acid assay it is provided for a plurality of amplification reactions or PCRs to be carried out in parallel or independently from one another using different primers S4 to S6 and/or primer pairs, such that a large number of (different) analytes or target nucleic-acid sequences ZN can be amplified or copied in parallel and subsequently analyzed.

After carrying out the amplification reaction(s), corresponding fluid volumes and/or sample portions and/or amplification products are conducted out of the reaction cavities 109 in succession to the sensor arrangement, in particular the sensor apparatus 113 and/or the sensor compartment 118, in particular via a group-specific and/or separate intermediate cavity 106E, 106F or 106G (respectively) and/or via the optional (common) intermediate temperature-control cavity 110.

The intermediate cavities 106E to 106G may contain further reagents, in this case dry reagents S9 and S10, respectively, for preparing the amplification products for the hybridization, e.g., a buffer, in particular an SSC buffer, and/or salts for further conditioning. On this basis, further conditioning of the amplification products can be carried out, in particular in order to improve the efficiency of the subsequent hybridization (bonding to the capture molecules). Particularly preferably, the pH of the sample P is set or optimized in the intermediate cavities 106E to 106G and/or by means of the dry reagents S9 and S10.

Optionally, the sample P or sample portions, the analytes, amplification products and/or target nucleic-acid sequences ZN is/are, in particular immediately before being fed to the sensor arrangement or sensor apparatus 113 and/or between the reaction cavities 109 and the sensor arrangement or sensor apparatus 113, actively temperature-controlled (in advance), preferably preheated, in particular by means of and/or in the intermediate temperature-control cavity 110 and/or by means of the intermediate temperature-control apparatus 204B, particularly preferably in order to denature the analytes, amplification products and/or target nucleic-acid sequences ZN.

After the (heated) sample P and/or the analytes and/or amplification products are fed to the sensor apparatus 113, the analytes and/or amplification products are hybridized to the capture nucleic-acid sequences FN, preferably by (actively) temperature-controlling, in particular heating, the sensor arrangement or sensor apparatus 113, in particular by means of the sensor temperature-control apparatus 204C, as shown in FIG. 9.

By feeding the (heated) sample P and/or the analytes and/or the amplification products to the sensor apparatus 113 and/or by (actively) temperature-controlling, in particular heating, the sensor arrangement or sensor apparatus 113, in particular by means of the sensor temperature-control apparatus 204C, the capture molecules, in particular the capture nucleic-acid sequences, preferably the hairpin probes HS, are denatured and opened.

FIG. 6 schematically shows different capture molecules, in particular capture nucleic-acid sequences, in the form of hairpin probes HS1 to HS4, which are assigned to different sensor fields 113B. FIG. 6 shows the closed, i.e., non-hybridized and undenatured, state of the hairpin probes HS1 to HS4, which are each provided with a label so as to directly or indirectly detect an analyte, here a target nucleic acid ZN.

Figure 7:
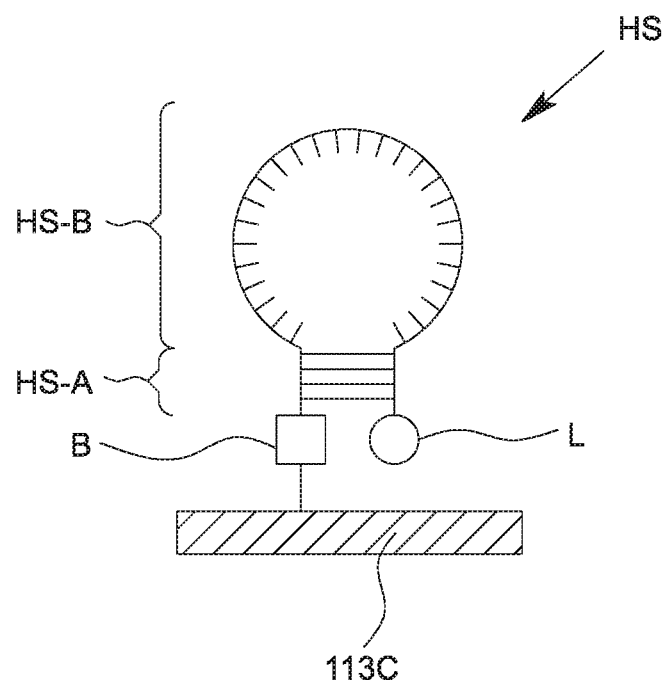
FIG. 7 shows a hairpin probe of the sensor apparatus in the closed state.
Figure 8:
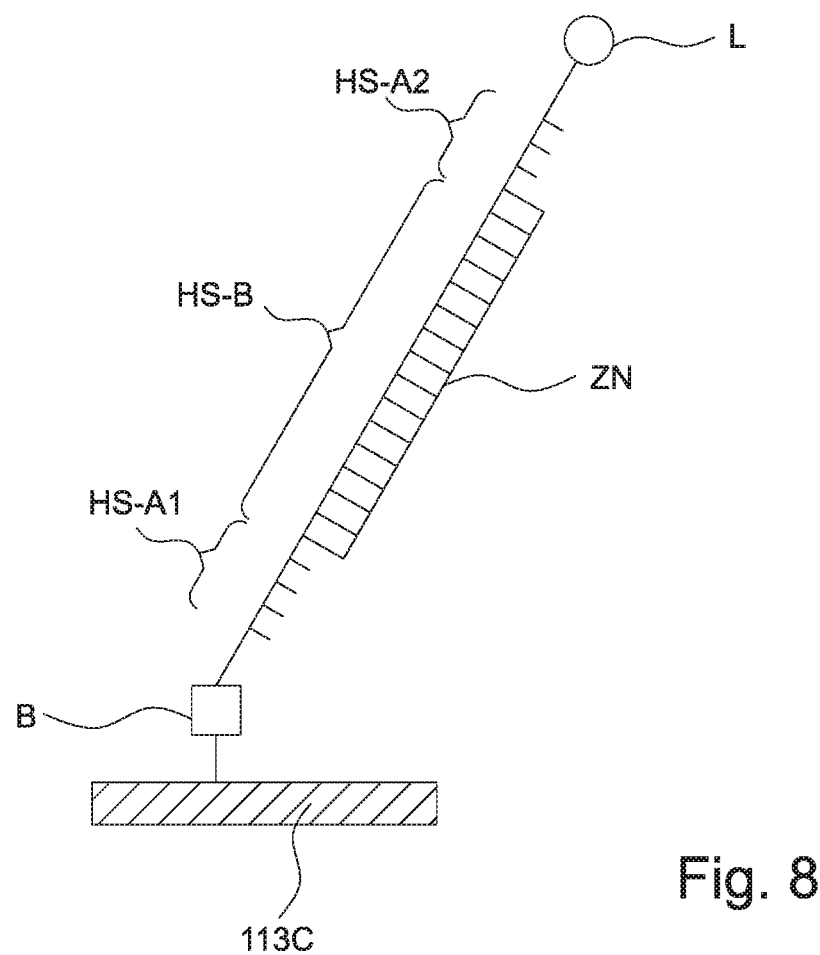
FIG. 8 shows a hairpin probe of the sensor apparatus in the open and hybridized state.

By feeding the (heated) sample P and/or by temperature-controlling the sensor apparatus 113, in particular by means of the temperature-control apparatus 204C, the hairpin probes HS are denatured, i.e., the intramolecular hydrogen bonds of the hairpin structures or stem-loop structures are broken, such that the hairpin probes open or are opened completely and are made available for bonding, in particular hybridization, to the analytes, in particular target nucleic-acid sequences ZN. In FIG. 9, different target analytes are represented, by way of example, by target nucleic-acid sequences ZN1, ZN3 and ZN4. FIG. 7 and FIG. 8 show in greater detail the exact construction and the mode of operation of capture molecules which are preferably used according to the invention and are in the form of hairpin probes HS.

The target nucleic-acid sequences ZN1, ZN3 and ZN4 shown in FIG. 9 shall be capable of bonding to the hairpin probes HS1, HS3 and HS4, i.e., in the selected example, no analyte is available for hybridization in the case of hairpin probe HS2.

For hybridization, a temperature which is optimum for hybridization in each case is set in particular by means of the temperature-control apparatus 204C, the temperature in particular running through a special temperature regime, which is preferably in the form of a temperature gradient. The temperature gradient is preferably designed such that the temperature is slowly and continuously lowered from the denaturing temperature, which is usually in the range of between 95 and 100° C., to values from 50 to 60° C., since the preferred hybridization temperatures of the nucleic acid are in the range of between 95 or 100° C. and 50 to 60° C.

As shown in FIG. 10, the target nucleic-acid sequences ZN1, ZN3 and ZN4 bond to the hairpin probes HS1, HS3 and HS4, respectively, whereas the hairpin probe HS2 is not hybridized and closes again when falling below the denaturing temperature, such that the label L of the hairpin probe HS2 is not available for detection. The sensor field 113B to which the hairpin probe HS2 is assigned will thus not supply a signal or will supply a signal that is different to that supplied by the hybridized hairpin probes HS1, HS3 and HS4.

FIG. 7 shows a capture molecule according to the invention in the form of a hairpin probe HS in the closed state. The hairpin probe HS consists of a single-strand nucleic-acid sequence which is subdivided into or comprises the stem HS-A and the loop HS-B. When the hairpin probe HS is not bonded to a target nucleic acid ZN and is undenatured, the nucleic-acid portions of the stem HS-A are interconnected by intramolecular bonds, in particular hydrogen bonds, such that a hairpin structure or stem-loop structure is obtained with the nucleic-acid portion of the loop, and the capture molecule is not available for hybridization.

The hairpin probe HS is preferably bonded to a bonding unit B via the stem. The hairpin probe HS is preferably connected to a substrate, in particular a sensor field 113C via said bonding unit B.

The label L is preferably located on the end of the stem HS-A that is opposite the bonding unit B, by means of which label L it is possible to detect different states of the hairpin probe HS, in particular the difference between an open, in particular hybridized, and a closed, i.e., non-hybridized, state of the hairpin probes HS.

FIG. 8 shows the hairpin probe HS shown in FIG. 7 in the open, i.e., hybridized, state, a nucleic-acid sequence ZN bonding to the nucleic-acid portion of the loop HS-B. The nucleic-acid portions HS-A1 and HS-A2 of the stem HS-A are arranged ahead of and after the nucleic-acid portion HS-B of the loop, the nucleic-acid portions and the loop together forming a single-strand nucleic-acid sequence.

When the capture nucleic acid is in the state shown in this figure, the label L is far apart from the surface of the sensor field 113C and is neither sterically shielded by means of the surface of the sensor field 113C nor by means of the hairpin probe HS, in particular the loop HS-B, and can preferably react with further molecules, in particular detector molecules D, as a result of which the target nucleic-acid sequence can be detected or identified.

Once the sample P, analytes and/or amplification products are hybridized and/or bonded to the capture nucleic-acid sequences FN, in particular hairpin probes HS, detection follows, in particular by means of the label L provided by the capture molecules, or in another manner, as shown in FIG. 11.

In the following, a particularly preferred variant of the detection is described in greater detail, specifically electrochemical detection or detection by means of redox cycling, but other types of detection, for example optical or capacitive detection, may also be carried out.

Following the (respective) bonding/hybridization of the analytes, the sensor arrangement and/or sensor apparatus 113 is prepared and/or pretreated for the detection.

Following the bonding of the analytes, preferably an optional washing process takes place and/or additional reagents or liquids, in particular from the storage cavities 108B to 108E, are optionally fed in.

In particular, it may be provided that remnants of the sample P, or sample residues, or unbonded analytes or amplification products, reagents and/or remnants from the PCR, and other substances that may disrupt the further method sequence, are in particular removed from the sensor compartment 118.

Particularly preferably, a washing process for the sensor arrangement or sensor apparatus 113 is a process and/or method step in which a fluid, in particular a wash buffer, is conducted through the sensor compartment 118 and/or past the sensor apparatus 113, in particular in order to wash away or flush out unbonded analytes from the sensor compartment 118 and/or the region of the sensor apparatus 113. In this case, the wash buffer itself preferably does not comprise any analytes, and therefore the sensor compartment 118 is freed of substances that could prevent or distort a subsequent evaluation.

Washing or flushing may in particular take place using a fluid or reagent F3, in particular a wash buffer, particularly preferably a sodium-citrate buffer or SSC buffer, which is preferably contained in the storage cavity 108C. Unbonded analytes, amplification products and substances which could disrupt subsequent detection are preferably removed from the sensor compartment 118 and/or from the sensor apparatus 113 by the wash buffer and/or fed to the collection cavity 111.

Subsequently and/or after the washing process, in accordance with a preferred variant of the method, detection of the analytes and/or amplification products bonded to the capture molecules takes place.

In order to detect the analytes or amplification products bonded to the capture molecules, a reagent F4 and/or detector molecules D, in particular alkaline phosphatase/streptavidin, is/are fed to the sensor apparatus 113, preferably from the storage cavity 108D.

Within the meaning of the present invention, the term "detector molecules" is preferably understood to mean molecules that bond specifically to the marker or label L of the capture molecules, in particular hairpin probes HS, and thus allow the detection thereof.

In particular, the detector molecules D may be enzyme conjugates and/or immunoconjugates, which bond specifically to the marker or label L, in particular biotin, and comprise a reporter enzyme for converting a substrate SU.

In the context of the present invention, the detector molecules D are preferably based on streptavidin, which has a high affinity for biotin, and/or alkaline phosphatase, which can convert non-reactive phosphate monoesters to electrochemically active molecules and phosphate.

Preferably, a detection system is used, where the label L is based on biotin and where the detector molecules D are based on streptavidin/alkaline phosphatase. However, other detector molecules D can also be used.

The reagents F4 or detector molecules D can bond to the bonded analytes or amplification products, in particular to the label L of the bonded analytes or amplification products, particularly preferably to the biotin marker, as shown in FIGS. 10 and 11.

Optionally, subsequently or after the reagents F4 and/or detector molecules D have bonded to the analytes and/or amplification products or the labels L, an (additional) washing process and/or flushing takes place, preferably by means of the fluid or reagent F3 or wash buffer, in particular in order to remove unbonded reagents F4 and/or detector molecules D from the sensor apparatus 113.

Preferably, a reagent S7 and/or S8 and/or substrate SU for the detection, in particular from the storage cavity 106D, is lastly fed to the sensor arrangement or sensor apparatus 113, preferably together with a fluid or reagent F2 (in particular a buffer), which is suitable for the substrate SU, particularly preferably for dissolving the reagent S7 and/or S8 and/or substrate SU, the fluid or reagent F2 in particular taken from the storage cavity 108B. In particular, the reagent S7 and/or S8 can form or can comprise the substrate SU.

Preferably, p-aminophenyl phosphate (pAPP) is used as the substrate SU.

The substrate SU preferably reacts on and/or with the bonded analytes or amplification products and/or detector molecules D and/or allows these to be electrochemically measured.

In order to carry out the detection or electrochemical measurement of the bonded analytes or amplification products or after adding the substrate SU, the sensor cover 117 is preferably pneumatically actuated and/or lowered onto the sensor apparatus 113 (as shown in FIG. 11), in particular in order to fluidically separate the (individual) sensor fields 113B from one another, and/or to prevent or minimize the exchange of substances between the sensor fields 113B.

Actuating or lowering the sensor cover 117 in particular prevents a reaction and/or detection from being assigned to an incorrect or adjacent sensor field 113B, and in this way prevents measurement inaccuracies or errors from occurring. In particular, the sensor cover 117 increases the measurement accuracy of the method.

As shown in particular in FIG. 11, the substrate SU is preferably split by the bonded detector molecules D, in particular the alkaline phosphatase of the bonded detector molecules D, preferably into a first substance SA, such as p-aminophenol, which is in particular electrochemically active and/or redox active, and a second substance SP, such as phosphate.

Preferably, the first or electrochemically active substance SA is detected in the sensor apparatus 113 or in the individual sensor fields 113B by electrochemical measurement and/or redox cycling.

Particularly preferably, by means of the first substance SA, a redox reaction takes place at the electrodes 113C, the first substance SA preferably discharging electrons to or receiving electrons from the electrodes 113C.

In particular, the presence of the first substance SA and/or the respective amounts in the respective sensor fields 113B is detected by the associated redox reactions. In this way, it can be determined qualitatively and in particular also quantitatively whether and how many analytes or amplification products are bonded to the capture molecules in the respective sensor fields 113B. This accordingly gives information on which analytes are or were present in the sample P, and in particular also gives information on the quantity of said analytes.

In particular, by means of the redox reaction with the first substance SA, an electrical signal is generated at the assigned electrodes 113C, the signal preferably being detected by means of an assigned electronic circuit.

Depending on the signal from the electrodes 113C that is generated in this way, it is determined whether and/or where hybridization to the capture molecules has occurred.

After the test has been carried out, the cartridge 100 is disconnected from the analysis device 200 and/or is released or ejected therefrom, and is in particular disposed of.

Individual aspects and features of the present invention and individual method steps and/or variants of the method may be implemented independently from one another, but also in any desired combination and/or order.

Exemplary Embodiments

In order to test the effectiveness of the analysis system according to the invention, single-strand nucleic-acid sequences which form hairpin structures and are labelled at one end with biotin are immobilized and tested on the sensor fields of a sensor apparatus as hybridization probes in the form of hairpin probes. At the end of the nucleic-acid sequence that is remote from the label, the hairpin probes comprise a C6 unit having a thiol, in order to provide for bonding to the gold surface of a sensor apparatus.

The hairpin probes are spotted in different sensor fields of the sensor apparatus of an analysis system according to the invention. In order to test the efficiency of the system according to the invention, sensor fields are spotted with different solutions. 3'-biotinylated nucleic-acid sequences and 5'-biotinylated nucleic-acid sequences are used as hairpin probes which are each inserted in different sensor fields of the sensor apparatus at different concentrations of 100 nmol/l, 50 nmol/l and 10 nmol/l, respectively. The sensor fields are spotted with a hybridization buffer (3×SSC) as the negative control and a biotinylated strand is spotted on the sensor fields as the positive control.

The 5'-biotinylated hairpin probe has the following structure (SEQ ID No. 1): thiol-C6-ACC AG CCTGC TAG ACA ATG TTG CCG TTC GAC TTG C GCAGG-biotin.

The 3'-biotinylated hairpin probe has the following structure (SEQ ID No. 2): biotin-ACC AG CCTGC TAG ACA ATG CTG CCG TTC GAC TTG C GCAGG-thiol-C6.

Subsequently, a hybridization buffer (3×SSC), a complementary counter-strand comprising the nucleic-acid sequence (SEQ ID No. 3) AACACAACAATACTGT-TYGARGTCCACC in concentrations of 1 nmol/l, 10 nmol/l and 100 nmol/l or a non-complementary counter-strand (N2) is pumped into the sensor fields.

Figure 12:
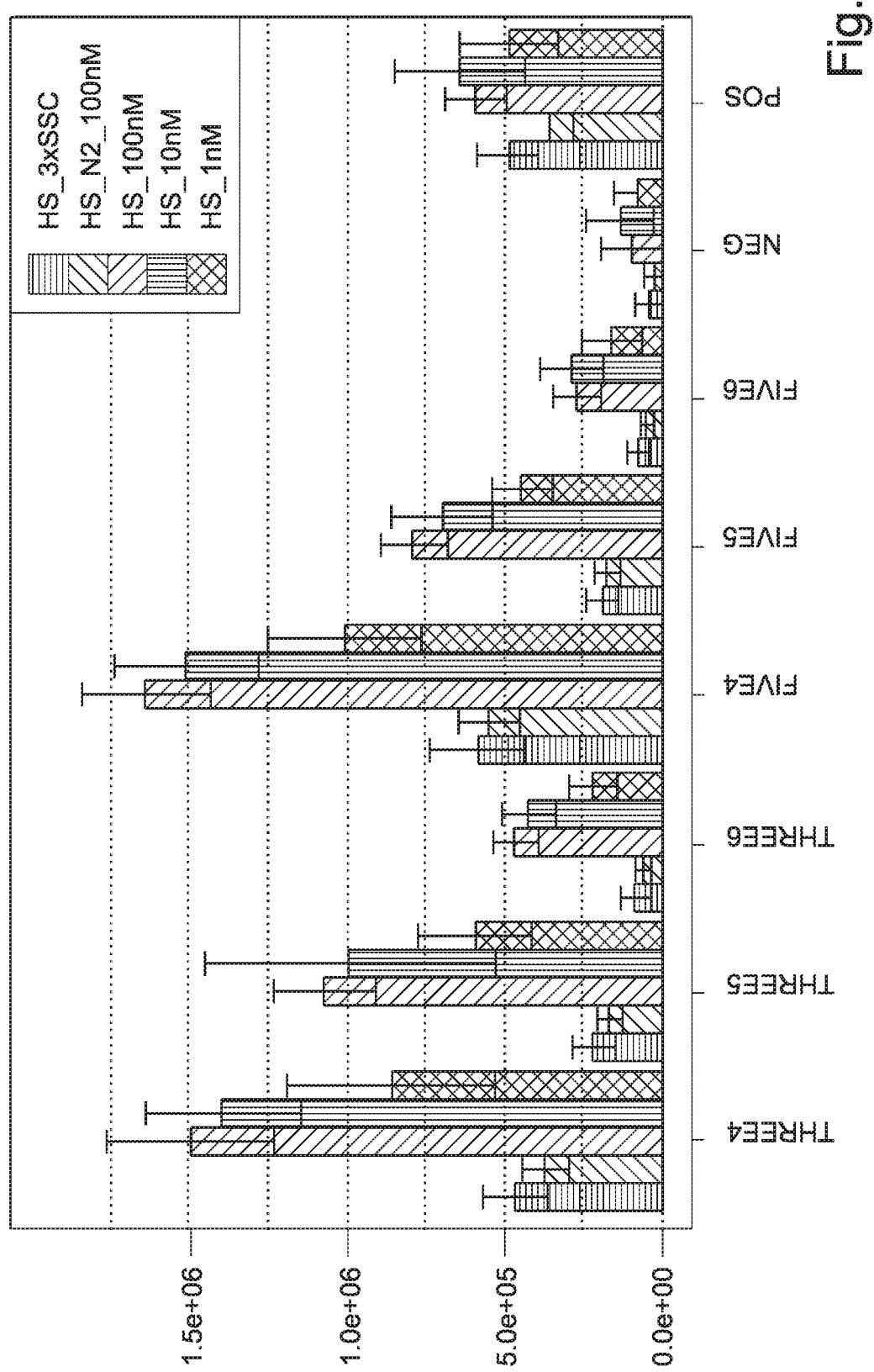
FIG. 12 shows the results of an electrical measurement on various test systems.

In order to denature the hairpin probes and to set or adjust the optimal respective hybridization temperatures, a temperature gradient is used in which the sensor field is heated to 95° C. and then cooled to 50° C. Subsequently, the substrate p-aminophenol phosphate (pAPP) is converted to p-aminophenol and phosphate by means of the conjugate streptavidin/alkaline phosphatase as a detector molecule after bonding to the biotin label, and the redox-active p-aminophenol is electrochemically detected. The results of the electrochemical measurement are shown in FIG. 12:

In FIG. 12, the designations THREE4 to THREE6 represent 3'-biotinylated hairpin probes which have been spotted on the sensor fields in a concentration of 100 nmol/l (THREE4), 50 nmol/l (THREE5) and 10 nmol/l (THREE6), respectively. The designations FIVE4 to FIVE6 represent the corresponding 5'-biotinylated hairpin probes. FIVE4 corresponds to a concentration of the 5'-biotinylated hairpin probe of 100 nmol/l, FIVE5 to a concentration of 50 nmol/l and FIVE6 to a concentration of 10 nmol/l, respectively. NEG corresponds to spotting with a hybridization buffer and constitutes the negative control, whereas POS represents the positive control.

It can be seen from the graph that the negative control remains significantly below the value of the positive control used. An increase in the concentration of spotted probes in the sensor fields results in an increased signal, and the same applies to the increase in the suitable strand in the applied solution. In the case of an unsuitable subject (N2), the signal remains in the range of the hybridization buffer without a counter-strand. This demonstrates that a signal is generated, selectively, only if there is also a suitable counter-strand which prevents the hairpin probes from closing.

What is claimed is:

1. A sensor apparatus for testing a biological sample, comprising:
   a measuring site comprising a sensor array having a plurality of sensor cavities and/or sensor fields, wherein the sensor apparatus comprises barriers between each of the sensor cavities and/or fields,
   at least one capture molecule for bonding an analyte, the capture molecule being a hairpin probe bonded to a surface of the sensor cavities and/or fields of a sensor field of the sensor apparatus and comprising a nucleic-acid sequence for bonding the analyte and
   a label for detecting the analyte, wherein the label is reactable with enzyme conjugates which in turn convert substrates which can be detected by means of electrochemical measurements,
   wherein the sensor apparatus is configured to adjust the temperature in a dynamic temperature regime for bonding the analyte to the capture molecule,
   wherein a starting temperature of the temperature regime is a value ranging from 70 to 95° C. and an end temperature of the temperature regime is a value ranging from 50 to 60° C.

2. The sensor apparatus according to claim 1, wherein the analyte is a target nucleic-acid sequence.

3. The sensor apparatus according to claim 1, wherein the capture molecule is bonded to the surface of the sensor apparatus by means of a bonding unit.

4. The sensor apparatus according to claim 1, wherein the label is able to assume at least two distinguishable states by at least one of chemical and physical methods.

5. The sensor apparatus according to claim 1, wherein the label is able to assume different states depending on bonding of an analyte.

6. The sensor apparatus according to claim 5, wherein the different states of the label are detectable or identifiable by at least one of chemical and physical methods selected from the group of electrical measurements and electrochemical methods.

7. The sensor apparatus according to claim 1, wherein the barriers between each of the sensor cavities and/or fields are formed by a hydrophobic layer having corresponding recesses for the sensor cavities and/or fields.

8. The sensor apparatus according to claim 1, wherein the label is biotin, wherein the biotin is arranged in a manner enabling the biotin to bond a streptavidin enzyme conjugate which converts detectable substrates.

9. The sensor apparatus according to claim 1, wherein the sensor apparatus is constructed in a manner usable in a mobile point-of-care systems.

10. An analysis system for testing a biological sample containing at least one analyte,
   the system comprising a sensor apparatus comprising
      a measuring site comprising a sensor array having a plurality of sensor cavities and/or sensor fields, wherein the sensor apparatus comprises barriers between each of the sensor cavities and/or fields,
at least one capture molecule for bonding the analyte,
the at least one capture molecule being bonded to a surface of the sensor cavities and/or fields of the sensor apparatus and comprising a label for detecting the analyte,
wherein the at least one capture molecule is a hairpin probe and comprises a nucleic-acid sequence for bonding the analyte,
wherein the label is reactable with enzyme conjugates which in turn convert substrates which are detectable by means of electrochemical measurement,
the system further comprising a temperature control apparatus assigned to the sensor apparatus, configured to adjust the temperature in a dynamic temperature regime for bonding the analyte to the capture molecule, wherein a starting temperature of the temperature regime is a value ranging from 70 to 95° C. and an end temperature of the temperature regime is a value ranging from 50 to 60° C.

11. The analysis system according to claim 10, wherein the barriers between each of the sensor cavities and/or fields are formed by a hydrophobic layer having corresponding recesses for the sensor cavities and/or fields.

12. The analysis system according to claim 10, wherein the label is biotin, wherein the biotin is arranged in a manner enabling the biotin to bond a streptavidin enzyme conjugate which converts detectable substrates.

13. The analysis system according to claim 10, wherein the analysis system is constructed for use as a mobile point-of-care system.

14. A sensor apparatus for direct integration in mobile point-of-care systems for testing a biological sample, comprising:
at least one capture molecule for bonding an analyte, the capture molecule being a hairpin probe bonded to a surface of the sensor apparatus comprising a nucleic-acid sequence for bonding the analyte and
a label for detecting the analyte, wherein the label can react with enzyme conjugates which in turn convert substrates, which can be detected by means of electrochemical measurements,
wherein the sensor apparatus is configured to adjust the temperature in a dynamic temperature regime for bonding the analyte to the capture molecule,
wherein a starting temperature of the temperature regime is a value ranging from 70 to 95° C. and an end temperature of the temperature regime is a value ranging from 50 to 60° C.
wherein the sensor apparatus is plate-shaped, and wherein the surface area of a flat side of the sensor apparatus is less than 300 mm$^2$ and greater than 0.25 mm$^2$.

15. The sensor apparatus according to claim 14, wherein the sensor apparatus comprises a measuring site comprising a sensor array having a plurality of sensor cavities and/or sensor fields, wherein the sensor apparatus comprises barriers between each of the sensor cavities and/or fields,
wherein the barriers between each of the sensor cavities and/or fields are formed by a hydrophobic layer having corresponding recesses for the sensor cavities and/or fields.

16. The sensor apparatus according to claim 14, wherein the label is biotin, wherein the biotin is arranged in a manner enabling the biotin to bond a streptavidin enzyme conjugate which converts detectable substrates.

17. An analysis system for testing a biological sample being a mobile point-of-care system containing at least one analyte,
the system comprising a sensor apparatus comprising at least one capture molecule for bonding the analyte,
the at least one capture molecule being bonded to a surface of the sensor apparatus comprising a label for detecting the analyte,
wherein the at least one capture molecule is a hairpin probe and comprises a nucleic-acid sequence for bonding the analyte,
wherein the label is reactable with enzyme conjugates which in turn convert substrates, which can be detected by means of electrochemical measurements,
the system further comprising a temperature control apparatus assigned to the sensor apparatus, configured to adjust the temperature in a dynamic temperature regime for bonding the analyte to the capture molecule, wherein a starting temperature of the temperature regime is a value ranging from 70 to 95° C. and an end temperature of the temperature regime is a value ranging from 50 to 60° C.
wherein the sensor apparatus is plate-shaped, and wherein the surface area of a flat side of the sensor apparatus is less than 300 mm$^2$ and greater than 0.25 mm$^2$.

18. The analysis system according to claim 17, wherein the sensor apparatus of the analysis system comprises a measuring site comprising a sensor array having a plurality of sensor cavities and/or sensor fields, wherein the sensor apparatus comprises barriers between each of the sensor cavities and/or fields,
wherein the barriers between each of the sensor cavities and/or fields are formed by a hydrophobic layer having corresponding recesses for the sensor cavities and/or fields.

19. The sensor apparatus according to claim 17, wherein the label is biotin, wherein the biotin is arranged in a manner enabling the biotin to bond a streptavidin enzyme conjugate which converts detectable substrates.

* * * * *